US012596098B2

(12) United States Patent
Foret et al.

(10) Patent No.: US 12,596,098 B2
(45) Date of Patent: Apr. 7, 2026

(54) DEVICE FOR VOLUME COUPLING IN EPITACHOPHORESIS

(71) Applicant: Roche Sequencing Solutions, Inc., Pleasanton, CA (US)

(72) Inventors: Frantisek Foret, Brno (CZ); Ivona Voracova, Brno (CZ); Jan Prikryl, Brno (CZ); Jakub Novotny, Orlova-Lutyne (CZ)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 259 days.

(21) Appl. No.: 18/556,327

(22) PCT Filed: Apr. 20, 2022

(86) PCT No.: PCT/US2022/025530
§ 371 (c)(1),
(2) Date: Oct. 19, 2023

(87) PCT Pub. No.: WO2022/226056
PCT Pub. Date: Oct. 27, 2022

(65) Prior Publication Data
US 2024/0201133 A1 Jun. 20, 2024

Related U.S. Application Data

(60) Provisional application No. 63/177,637, filed on Apr. 21, 2021.

(51) Int. Cl.
*G01N 27/447* (2006.01)
*C12Q 1/6806* (2018.01)

(52) U.S. Cl.
CPC ..... *G01N 27/44773* (2013.01); *C12Q 1/6806* (2013.01)

(58) Field of Classification Search
CPC ........................ G01N 27/44773; C12Q 1/6806
See application file for complete search history.

(56) References Cited

U.S. PATENT DOCUMENTS 3,640,813 A * 2/1972 Nerenberg ....... G01N 27/44704
204/615
2020/0282392 A1 9/2020 Astier et al.

OTHER PUBLICATIONS

NASA "Phases of Matter", May 13, 2021, https://www.grc.nasa.gov/www/k-12/airplane/state.html (Year: 2021).*

(Continued)

*Primary Examiner* — Alexander S Noguerola
(74) *Attorney, Agent, or Firm* — Kilpatrick Townsend & Stockton LLP

(57) ABSTRACT

Epitachophoresis (ETP) methods and devices that improve concentrating samples and/or separating components of samples. ETP methods and devices allow for electromigration in two dimensions. Electromigration of a sample may first occur in a first dimension along a single plane. Electromigration may then continue in a second dimension, which may be different from the first dimension. The volume where the electromigration occurs may significantly reduce from the first dimension to the second dimension. This smaller dimension may allow for increased concentration of samples or improved separation of components of a sample.

20 Claims, 13 Drawing Sheets

(56) References Cited

OTHER PUBLICATIONS

Edward Southern, "Gel Electrophoresis of Restriction Fragments," Chapter 9, pp. 152-176, in Methods of Enzymology, vol. 68, Academic Press, 1979 (Year: 1979).*

International Search Report and Written Opinion in International Appln. PCT/US2022/025530 mailed Jul. 8, 2022; 12 pages.

Foret et al.; "Macrofluidic Device for Preparative Concentration Based on Epitachophoresis"; *Analytical Chemistry*; vol. 91, No. 11; Jun. 4, 2019; pp. 7047-7053.

* cited by examiner

700

1100

1110 — Apply a voltage difference between a first electrode and a second electrode 1120 — Flow, using the voltage difference, a component from a sample in a first channel in a first direction 1130 — Flow, in the second channel, the component focused in the band in a second direction 1140 — Collect the second mixture in the vessel while applying the voltage difference

DEVICE FOR VOLUME COUPLING IN EPITACHOPHORESIS

CROSS-REFERENCE TO RELATED PATENT APPLICATIONS

The present application claims benefit of priority to U.S. Provisional Patent Application No. 63/177,637, filed Apr. 21, 2021, which is incorporated herein by reference for all purposes.

TECHNICAL FIELD

The present disclosure relates to the field of electrophoresis for sample analysis and relates to analysis of biological samples by selective separation, detection, extraction, isolation, purification, and/or (pre-) concentration of samples, through devices and methods for epitachophoresis.

BACKGROUND

Electrophoresis approaches have been used to separate and analyze samples for a variety of purposes, such as for identifying a particular substance or for determining the size and type of molecules in a solution. For example, a variety of molecular biology applications have employed electrophoresis to separate proteins or nucleic acids, determine molecular weight, and/or prepare samples for further analysis. In these and other applications, electrophoresis generally involves the movement of an electrically-charged substance (e.g., molecules or ions) under the influence of an electric field. This movement can facilitate the separation of a sample from other samples or substances. Once separated, the sample may readily be analyzed using an optical or other approach.

A variety of electrophoresis-based approaches typically are used in connection with different applications dependent on the particular needs of the analysis that to be performed. For example, isotachophoresis ("ITP") is a concentration and separation technique which leverages electrolytes with different electrophoretic mobility to focus, and in some cases separate, ionic analytes into distinct zones ("focused zones"). In ITP, analytes simultaneously focus and separate between high effective mobility leading electrolyte ("LE") ions and low effective mobility trailing electrolyte ("TE") ions. The balance of electromigration and diffusion at the zone boundaries in ITP typically results in sharp moving boundaries.

Conventionally, ITP is effected through use of devices and methods that feature capillary or microfluidic channel designs. Such devices and methods are capable of handling only small volumes (μl scale) of sample for analysis, which can make the analysis of biological samples, such as the extraction of nucleic acids from blood and/or plasma, difficult. As such, further development of devices and methods for analyzing samples that may have large volumes would likely be beneficial. Additionally, concentrating samples in small volumes may be advantageous. Epitachophoresis (ETP) methods and devices that provide these and other improvements are described herein.

BRIEF SUMMARY

The present disclosure describes epitachophoresis (ETP) methods and devices that improve concentrating samples and/or separating components of samples. ETP methods and devices allow for electromigration in two dimensions. Electromigration of a sample may first occur in a first dimension along a single plane. Electromigration may then continue in a second dimension, which may be different from the first dimension. The volume where the electromigration occurs may significantly reduce from the first dimension to the second dimension. This smaller dimension may allow for increased concentration of samples or improved separation of components of a sample.

Some embodiments include a method of concentrating a component from a sample. A system may apply a voltage difference between a first electrode and a second electrode. The first electrode is disposed in a first mixture comprising a first electrolyte and the sample. The second electrode is disposed in a second electrolyte. The first electrolyte is discontinuous with the second electrolyte. The first mixture is in contact with the second electrolyte. The system may flow, using the voltage difference, the component in a first channel in a first direction. The first direction is away from the first electrode and to a second channel. The component is focused into a band. The first mixture is characterized as having a first thickness perpendicular to the first direction. The system may flow, in the second channel, the component focused in the band in a second direction. The second electrolyte is in the second channel. The second direction is from the first channel to an orifice of a vessel. The second channel is an annular space. A second mixture including the component and the second electrolyte in the second channel is characterized as having a second thickness perpendicular to the second direction. The first thickness is greater than the second thickness. The system may collect the second mixture in the vessel while applying the voltage difference. The concentration of the component in the second mixture in the vessel is higher than the concentration of the component in the sample.

In some aspects, a system for concentrating components in a sample includes a base defining a first channel and a cavity, a first electrode disposed in the first channel, and a second electrode. The first channel is in fluid communication with the cavity. An outer diameter of the first channel is greater than a first outer diameter at the top of the cavity. The cavity may have a conical shape with the first outer diameter being greater than a second outer diameter at the bottom of the cavity. The second electrode is configured to be in closer electrical communication with the cavity than with the first channel when the first channel and the cavity contain an electrolyte. The first channel is characterized by a first volume. The cavity may be configured to receive a vessel and to form a second channel when the vessel is disposed in the cavity. The second channel may be an annular space. The annular space may be defined by a surface of the base and a surface of the vessel when the vessel is disposed in the cavity. The second channel is characterized by a second volume. The first volume is greater than the second volume.

A better understanding of the nature and advantages of embodiments of the present disclosure may be gained with reference to the following detailed description and the accompanying drawings.

BRIEF DESCRIPTION OF THE DRAWINGS

In FIG. 2A, numbers 1-7 refer to the following: 1. Outer circular electrode; 2. Terminating electrolyte reservoir; 3. Leading electrolyte, optionally contained within a gel or otherwise hydrodynamically separated from the terminating electrolyte; 4. Leading electrolyte electrode/collection reservoir; 5. Central electrode; 6. Electric power supply; and 7. Boundary between leading and terminating electrolytes with sample ions focused in between; and the symbols r and d are used to represent the leading electrolyte reservoir radius and distance migrated by the LE/TE boundary, respectively.

In FIG. 2B, numbers 1-8 refer to the following: 1. Outer circular electrode; 2. Terminating electrolyte reservoir; 3. Leading electrolyte, optionally contained within a gel or otherwise hydrodynamically separated from the terminating electrolyte; 4. Leading electrolyte electrode/collection reservoir; 5. Center electrode; 6. Electric power supply; 7. Boundary between leading and terminating electrolytes with sample ions focused in between; and 8. Bottom support; and the symbols r and d are used to represent the leading electrolyte reservoir radius and distance migrated by the LE/TE boundary, respectively.

In FIG. 4, the numbers 1-10 refer to the following: 1. Outer circular electrode; 2. Terminating electrolyte reservoir; 3. Leading electrolyte, optionally contained within a gel or otherwise hydrodynamically separated from the terminating electrolyte; 4. Opening to leading electrolyte/collection reservoir; 5. Center electrode; 6. Electric power supply; 7. Boundary between leading and terminating electrolytes with sample ions focused in between; 8. Bottom support; 9. Tube connecting device to a leading electrolyte reservoir; 10. Leading electrolyte reservoir.

TERMS

Figure 1:
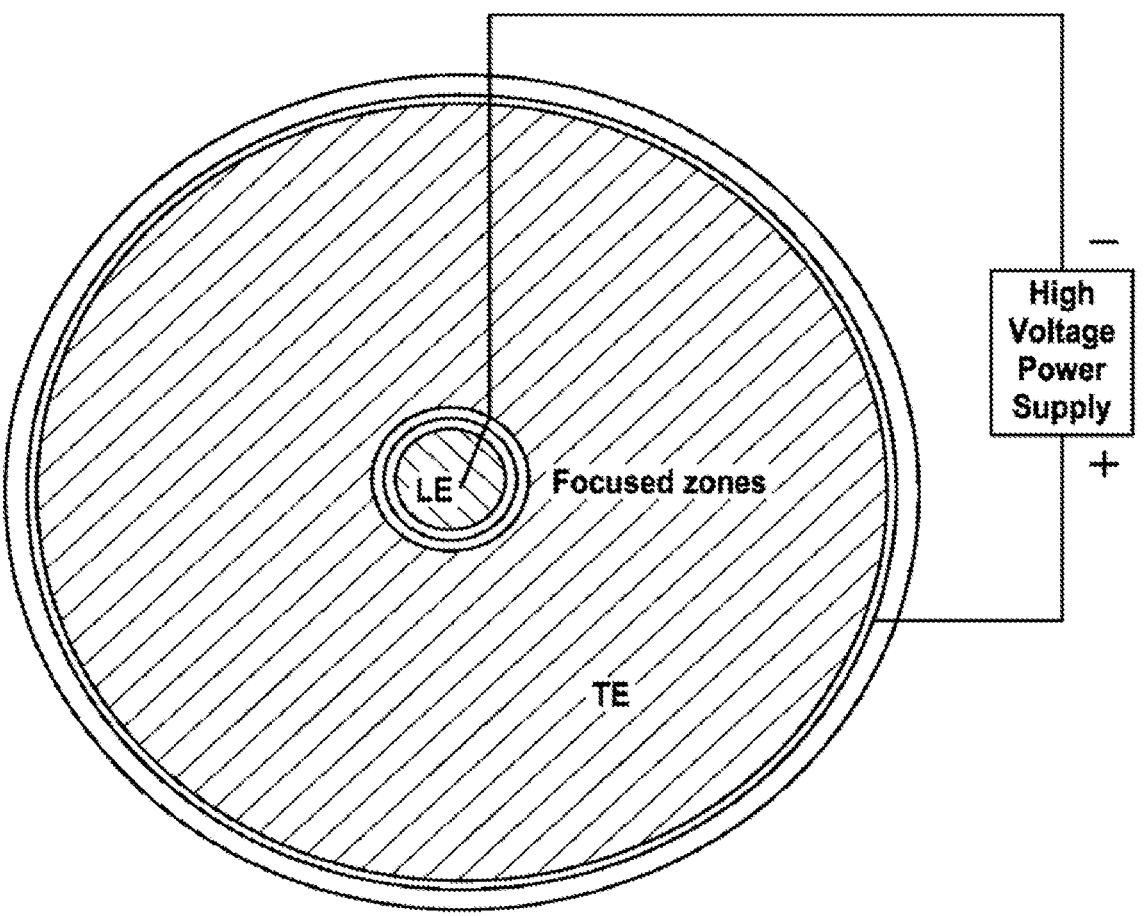
FIG. 1 provides a schematic representation of an exemplary device for effecting epitachophoresis.

As used herein, the term "isotachophoresis" generally refers to the separation of charged particles by using an electric field to create boundaries or interfaces between materials (e.g., between the charged particles and other materials in a solution). ITP generally uses multiple electrolytes, where the electrophoretic mobilities of sample ions are less than that of a leading electrolyte (LE) and greater than that of a trailing electrolyte (TE) that are placed in a device for ITP. The leading electrolyte (LE) generally contains a relatively high mobility ion, and a trailing electrolyte (TE) generally contains a relatively low mobility ion. The TE and LE ions are chosen to have effective mobilities respectively lower and higher than target analyte ions of interest. That is, the effective mobility of analyte ions is higher than that of the TE and lower than that of the LE. These target analytes have the same sign of charge as the LE and TE ions (i.e., a co-ion). An applied electric field causes LE ions to move away from TE ions and TE ions to trail behind. A moving interface forms between the adjacent and contiguous TE and LE zones. This creates a region of electric field gradient (typically from the low electric field of the LE to the high electric field of the TE). Analyte ions in the TE overtake TE ions but cannot overtake LE ions and accumulate ("focus" or form a "focused zone") at the interface between TE and LE. Alternately, target ions in the LE are overtaken by the LE ions; and also accumulate at interface. With judicious choice of LE and TE chemistry, ITP is fairly generally applicable, can be accomplished with samples initially dissolved in either or both the TE and LE electrolytes, and may not require very low electrical conductivity background electrolytes.

As used herein, the term "epitachophoresis" generally refers to methods of electrophoretic separation that are performed using a circular or spheroid and/or concentric device and/or circular and/or concentric electrode arrangement, such as by use of the circular/concentric and/or polygonal devices as described herein. Due to a circular/concentric or another polygonal arrangement that is used during epitachophoresis; unlike conventional isotachophoresis devices, the cross section area changes during migration of ions and zones, and the velocity of the zone movement is not constant in time due to the changing cross sectional area. Thus, an epitachophoretic arrangement does not strictly follow conventional isotachophoretic principles, wherein the zones migrate with constant velocities. Notwithstanding these significant differences as shown herein epitachophoresis can be used to efficiently separate and focus charged particles by using an electric field to create boundaries or interfaces between materials that may have different electrophoretic mobilities (e.g., between the charged particles and other materials in a solution). LE and TE, as described for use with ITP, can be used for epitachophoresis as well. In some embodiments, epitachophoresis may be effected using constant current, constant voltage, and/or constant power. In some embodiments, epitachophoresis may be effected using varying current, varying voltage, and/or varying power. In some embodiments, epitachophoresis may be effected within the context of devices and/or an arrangement of electrodes whose shape may be described in general as circular or spheroid, such that the basic principles of epitachophoresis may be accomplished as described herein. In some embodiments, epitachophoresis may be effected within the context of devices and/or an arrangement of electrodes whose shape may be described in general as polygons, such that the basic principles of epitachophoresis may be accomplished as described herein. In some embodiments, epitachophoresis may be effected by any non-linear, contiguous arrangement of electrodes, such as electrodes arranged in the shape of a circle and/or electrodes arranged in the shape of a polygon.

As used herein, the terms "in vitro diagnostic application (IVD application)", "in vitro diagnostic method (IVD method)", "in vitro diagnostic assay", and the like, generally refer to any application and/or method and/or device that may evaluate a sample for a diagnostic and/or monitoring purposes, such as identifying a disease in a subject, optionally a human subject. In some embodiments, said sample may comprise nucleic acids and/or target nucleic acids from a subject and/or from a sample, optionally further wherein said nucleic acids originated from a urine sample. In some embodiments, an epitachophoresis device may be used as an in vitro diagnostic device. In some embodiments, a target analyte that has been concentrated/enriched/isolated/purified through epitachophoresis may be used in a downstream in vitro diagnostic assay. In some embodiments, an in vitro diagnostic assay may comprise nucleic acid sequencing, e.g., DNA sequencing, e.g., RNA sequencing. In some embodiments, and IVD assay may comprise gene expression profiling. In some embodiments, an in vitro diagnostic method may be, but is not limited to being, any one or more of the following: staining, immunohistochemical staining, flow cytometry, FACS, fluorescence-activated droplet sorting, image analysis, hybridization, DASH, molecular beacons, primer extension, microarrays, CISH, FISH, fiber FISH, quantitative FISH, flow FISH, comparative genomic hybridization, blotting, Western blotting, Southern blotting, Eastern blotting, Far-Western blotting, Southwestern blotting, Northwestern blotting, and Northern blotting, enzymatic assays, ELISA, ligand binding assays, immunoprecipitation, ChIP, ChIP-seq, ChIP-ChIP, radioimmunoassays, fluorescence polarization, FRET, surface plasmon resonance, filter binding assays, affinity chromatography, immunocytochemistry, gene expression profiling, DNA profiling with PCR, DNA microarrays, serial analysis of gene expression, real-time polymerase chain reaction, differential display PCR, RNA-seq, mass spectrometry, DNA methylation detection, acoustic energy, lipidomic-based analyses, quantification of immune cells, detection of cancer-associated markers, affinity purification of specific cell types, DNA sequencing, next-generation sequencing, detection of cancer-associated fusion proteins, and detection of chemotherapy resistance-associated markers.

As used herein, the terms "leading electrolyte" and "leading ion" generally refer to ions having a higher effective electrophoretic mobility as compared to that of the sample ion of interest and/or the trailing electrolyte as used during ITP and/or epitachophoresis. In some embodiments, leading electrolytes for use with anionic epitachophoresis may include, but are not limited to including, chloride, sulphate and/or formate, buffered to desired pH with a suitable base, such as, for example, histidine, TRIS, creatinine, and the like. In some embodiments, leading electrolytes for use with cationic epitachophoresis may include, but are not limited to including, potassium, ammonium, and/or sodium with acetate or formate. In some embodiments, an increase of the concentration of the leading electrolyte may result in a proportional increase of the sample zone and a corresponding increase in electric current (power) for a given applied voltage. Typical concentrations generally may be in the 10-100 mM range; however, higher or lower concentrations may also be used.

As used herein, the terms "trailing electrolyte", "trailing ion", "terminating electrolyte", and "terminating ion" generally refer to ions having a lower effective electrophoretic mobility as compared to that of the sample ion of interest and/or the leading electrolyte as used during ITP and/or epitachophoresis. In some embodiments, trailing electrolytes for use with cationic epitachophoresis may include, but are not limited to including, MES, MOPS, acetate, glutamate and other anions of weak acids and low mobility anions. In some embodiments, trailing electrolytes for use with anionic epitachophoresis may include, but are not limited to including, reaction hydroxonium ion at the moving boundary as formed by any weak acid during epitachophoresis.

As used herein, the term "focused zone(s)" generally refers to a volume of solution that comprises a component that has been concentrated ("focused") as a result of performing epitachophoresis. A component may include a target analyte or any molecule having an ionic component affected by voltages applied in ETP. A focused zone may be collected or removed from a device, and said focused zone may comprise an enriched and/or concentrated amount of a desired sample, e.g., a target analyte, e.g., a target nucleic acid. In the epitachophoresis methods described herein the target analyte generally becomes focused in the center of the device, e.g., a circular or spheroid or other polygonal shaped device.

As used herein, the terms "band" and "ETP band" generally refer to a zone (e.g. focused zone) of ion, analyte, or sample that travels separately from other ions, analytes, or samples during electrophoretic (e.g., isotachophoretic, or epitachophoretic) migration. A focused zone within an epitachophoresis device may alternatively be referred to as an "ETP band". In some embodiments, an ETP band may comprise one or more types of ions, analytes, and/or samples. In some instances, an ETP band may comprise a single type of analyte whose separation from other materials present in a sample is desired, e.g., separation of target nucleic acid from cellular debris. In some instances, an ETP band may contain more than one target analyte, e.g., polypeptides or nucleic acids sequences highly similar in sequence, e.g., allelic variants. In some instances, the ETP band may comprise different analytes of similar size or electrophoretic mobility. In such instances, the more than one target analyte may be separated by further ETP runs, e.g., under different conditions that promote separation of said more than one analyte, and/or said more than one analyte may be separated by other techniques known in the art for separation of analytes, such as those described herein. In some embodiments, an ETP band may be collected and optionally subject to further analysis after one or more ETP-based isolations/purifications and collections. In some embodiments, an ETP band may comprise one or more target analytes undergoing or that have undergone ETP-based isolation/purification and optionally collection, e.g., as a part of an ETP-run.

The term "target nucleic acid" as used herein is intended to mean any nucleic acid to be detected, measured, amplified, isolated, purified, and/or subject to further assays and analyses. A target nucleic acid may comprise any single and/or double-stranded nucleic acid. Target nucleic acids can exist as isolated nucleic acid fragments or be a part of a larger nucleic acid fragment. Target nucleic acids can be derived or isolated from essentially any source, such as cultured microorganisms, uncultured microorganisms, complex biological mixtures, samples including biological samples, urine samples, tissues, sera, ancient or preserved tissues or samples, environmental isolates or the like. Further, target nucleic acids include or are derived from cDNA, RNA, genomic DNA, cloned genomic DNA, genomic DNA libraries, enzymatically fragmented DNA or RNA, chemically fragmented DNA or RNA, physically fragmented DNA or RNA, or the like. In some embodiments, a target nucleic acid may comprise a whole genome. In some embodiments, a target nucleic acid may comprise the entire nucleic acid content of a sample and/or biological sample, e.g., a urine sample. Target nucleic acids can come in a variety of different forms including, for example, simple or complex mixtures, or in substantially purified forms. For example, a target nucleic acid can be part of a sample that contains other components or can be the sole or major component of the sample. Also, a target nucleic acid can have either a known or unknown sequence.

The term "target microbe" as used herein is intended to mean any unicellular or multicellular microbe, found in blood, plasma, other body fluids, samples such as biological samples, and/or tissues, e.g., one associated with an infectious condition or disease. Examples thereof include bacteria, archaea, eukaryotes, viruses, yeasts, fungi, protozoan, amoeba, and/or parasites. Furthermore, the term "microbe" generally refers to the microbe that may cause a disease, whether the disease is referred to or the disease-causing microbe is referred to.

As used herein, the term "biomarker" or "biomarker of interest" refers to a biological molecule found in tissues, blood, plasma, urine, and/or other body fluids that is a sign of a normal or abnormal process, or of a condition or disease (such as cancer). A biomarker may be used to see how well the body responds to a treatment for a disease or condition. In the context of cancer, a biomarker refers to a biological substance that is indicative of the presence of cancer in the body. A biomarker may be a molecule secreted by a tumor or a specific response of the body to the presence of cancer. Genetic, epigenetic, proteomic, glycomic, and imaging biomarkers can be used for cancer diagnosis, prognosis, and epidemiology. Such biomarkers can be assayed in non-invasively collected biofluids like blood, serum, and/or urine. Biomarkers may be useful as diagnostics (e.g., to identify early stage cancers) and/or prognostics (e.g., to forecast how aggressive a cancer is and/or predict how a subject will respond to a particular treatment and/or how likely a cancer is to recur).

The term "sample" as used herein includes a specimen or culture (e.g., microbiological cultures) that includes or is presumed to include one or more target analytes. The term "sample" is also meant to include biological, environmental, and chemical samples, as well as any sample whose analysis is desired. A sample may include a specimen of synthetic origin. A sample may include one or more microbes from any source from which one or more microbes may be derived. A sample may include, but is not limited, to whole blood, skin, serum, plasma, umbilical cord blood, chorionic villi, amniotic fluid, cerebrospinal fluid, spinal fluid, lavage fluid (e.g., bronchioalveolar, gastric, peritoneal, ductal, ear, arthroscopic), tissue samples, biopsy samples, urine, feces, sputum, saliva, nasal mucous, prostate fluid, semen, lymphatic fluid, bile, organs, bone marrow, tears, sweat, breast milk, breast fluid, embryonic cells and fetal cells.

The term "target analyte" as used herein is intended to mean any analyte to be detected, measured, separated, concentrated, isolated, purified, and/or subject to further assays and analyses. In some embodiments, said analyte may be, but is not limited to, any ion, molecular, nucleic acid, biomarker, protein, cell, or population of cells, e.g., desired cells, and the like, whose detection, measurement, separation, concentration, and/or use in further assays is desired. In some embodiments, a target analyte may be derived from any of the samples described herein, e.g., a urine sample.

The term "communicate" is used herein to indicate a structural, functional, mechanical, electrical, optical, thermal, or fluidic relation, or any combination thereof, between two or more components or elements. As such, the fact that one component is said to communicate with a second component is not intended to exclude the possibility that additional components may be present between, and/or operatively associated or engaged with, the first and the second component.

As used herein, a "subject" refers to a mammalian subject (such as a human, rodent, non-human primate, canine, bovine, ovine, equine, feline, etc.) to be treated and/or one from whom a sample is obtained.

"Detecting" a sample within the context of an epitachophoresis device, system, or machine may comprise detecting its position at one, several, or many points throughout the device. Detection may generally occur by any one or more means that do not interfere with desired device, system, or machine function and with methods performed using said device, system, or machine. In some embodiments, detection encompasses any means of electrical detection, e.g., through the detection of conductivity, resistivity, voltage, current, and the like. Furthermore, in some embodiments, detection may comprise any one or more of the following: electrical detection, thermal detection, optical detection, spectroscopic detection, photochemical detection, biochemical detection, immunochemical detection, and/or chemical detection. In some embodiments, one or more target analytes may be detected during ETP-based isolation/purification and optionally collection of said one or more target analytes. Moreover, sample detection within the context of ETP devices and methods of ETP are further described in U.S. Application Ser. No. 62/744,984; US 2020/0282392 A1; and PCT Nos. PCT/EP2018/081049 and PCT/EP2019/077714, the entire contents of all of which are incorporated herein for all purposes.

In a sample analysis device or system, the term "sample collection volume" refers to a volume of sample intended for collection, e.g., by a robotic liquid handler, during or following analysis. In a device for effecting epitachophoresis, or a system comprising such a device, the sample collection volume is the volume intended for collection that comprises sample during or following epitachophoresis. In some embodiments, the sample collection volume may be located in the central well of a device or system described herein. In some embodiments, the sample collection volume may be located anywhere that permits collection of the desired sample. In some embodiments, the sample collection volume may be anywhere between the sample loading area and the leading electrolyte electrode/collection reservoir. The sample collection volume may be comprised by any suitable area, container, well, or space of the device or system. In some embodiments, the sample collection volume is comprised by a well, membrane, compartment, vial, pipette, or the like.

As used herein, the term "ETP-based isolation/purification" generally refers to devices and methods comprising ETP, e.g., devices on which ETP may be effected, e.g., methods comprising effecting ETP, wherein ETP focuses one or more target analytes into one or more focused zones (e.g., one or more ETP bands), thereby isolating/purifying the one or more target analytes from other materials comprised by an initial sample. It is noted the terms "isolate" and "purify" are used interchangeably. Furthermore, ETP based isolation/purification generally allows for subsequent collection of the one or more focused zones (one or more ETP bands) comprising said one or more target analytes. The degree of isolation/purification of one or more target analytes effected by one or more ETP-based isolations/purifications may be any degree or amount of isolation/purification of one or more target analytes from other materials. In some embodiments, ETP-based isolation/purification of a target analyte from a sample may result in 1% or less, 1% or more, 5% or more, 10% or more, 15% or more, 20% or more 25% or more, 30% or more, 35% or more, 40% or more, 45% or more, 50% or more, 55% or more, 60% or more, 65% or more, 70% or more, 85% or more, 90% or more, 95% or more, or 99% or more purity of said target analyte, e.g., as measured by an analytical technique to determine the composition of an ETP isolated/purified sample comprising one or more target analytes. In some embodiments, ETP-based isolation/purification of a target analyte from a sample may result in 1% or less, 1% or more, 5% or more, 10% or more, 15% or more, 20% or more 25% or more, 30% or more, 35% or more, 40% or more, 45% or more, 50% or more, 55% or more, 60% or more, 65% or more, 70% or more, 85% or more, 90% or more, 95% or more, or 99% or more of a target analyte being recovered from the original sample. In some embodiments, one or more ETP-based isolations/purifications may be effected to isolate/purify one or more target analytes, e.g., one or more nucleic acids. For example, in some instances, ETP-based isolation/purification may be effected on a sample comprising one or more target analytes to focus the one or more target analytes into one focused zone (ETP band), which substantially separates the one or more target analytes from other materials comprised in the original sample. The sample may be collected following ETP isolation/purification, and the isolated/collected sample may be further subject to another ETP-based isolation/purification. Optionally, the second ETP-based isolation-purification may be of such conditions so as to, in instances of more than one target analyte, isolate each of one or more target analytes into separate focused zones, each of which could optionally collected individually, thereby separating target analytes from one another, if desired.

As used herein, the term "mixed sample" generally refers to a sample comprising material from more than one source.

As used herein, the term "ETP upper marker" generally refers to a compound or molecule that is larger in size and/or longer in length as compared to a target nucleic acid, such that, during ETP-based isolation/purification and subsequent collection of a target analyte, the ETP upper marker indicates a cutoff point at which collection of the target analyte can be stopped. For example, fluorescently labeled, or otherwise detectably labeled, ETP upper maker can be generated of such a size that it is larger than a target DNA to be isolated/purified and collected during ETP-based isolation/purification. By monitoring the marker throughout the ETP run, the user or automated machine is able to stop the run before the marker falls into a collection tube, thereby allowing DNA smaller than the marker to be captured while larger contaminating DNA are left out as they are positioned behind the upper marker. Moreover, the ETP upper marker itself is not collected, and as such can be used at high quantity and with various detectable labels since it will not interfere with downstream assays, e.g., one or more IVD assays. In some instances, an ETP upper marker may be used in ETP-based isolation/purification methods as it aids in the exclusion of genomic DNA from an isolated/purified and collected sample of one or more target analytes.

DETAILED DESCRIPTION

In the practice of epitachophoresis (ETP), sample concentration and/or separation proceeds in a planar space. Components to be concentrated or separate move along one plane. Embodiments of the present invention include devices and methods that add dimensions to epitachophoretic separation. The first dimension is the electromigration along one plane, the first part of migration of the components. After the ETP focusing, the electromigration continues in a second dimension perpendicular or substantially perpendicular to the first dimension. This second migration proceeds in a space with at least 10 times lower volume than the first dimension. The term "volume coupling" is used to describe the reduction in volumes for electromigration in ETP.

Advantages of the ETP devices and methods include focusing the sample into a much lower volume, providing for a higher concentration of the sample. In addition, the smaller volume of the second separation dimension may allow for on-line connection to other analytical systems, including optical and electrochemical detection, separations including liquid chromatograph (LC), capillary electrophoresis (CE), NMR, and mass spectrometry.

I. Epitachophoresis

Devices for epitachophoresis generally use a concentric or polygonal disk architecture, for example, as depicted in FIG. 1-FIG. 4. Glass or ceramics may be used for fabrication of the system (i.e., material for concentric or polygonal disks) as these materials result in improved heat transfer properties that are beneficial during device operation. For example, as the flat channel of a epitachophoresis device has a favorable heat transfer capability compared to a narrow channel, over-heating (or boiling) of the focused material is generally prevented. Current/voltage programming is also suitable for adjusting the Joule heating of the device. Plastic materials may also be used for device fabrication. In general, devices are fabricated of such dimensions that accommodate a desired sample volume, such as milliliter-scale sample volumes, for example, up to 15 mL.

Figure 2A:
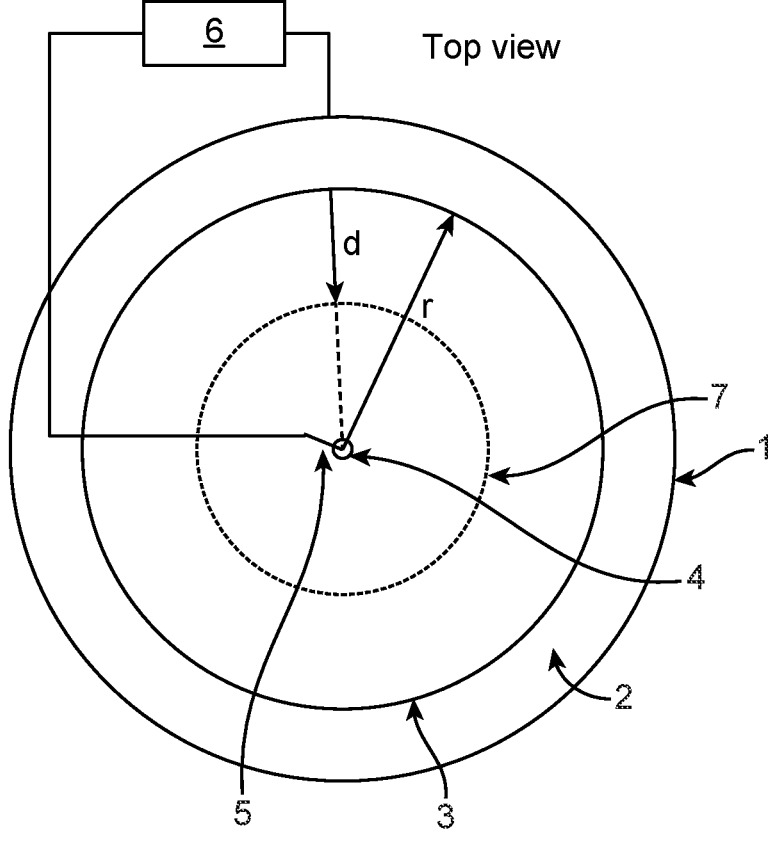
FIG. 2A provides a schematic representation of atop view of an exemplary device for effecting epitachophoresis.
Figure 2B:
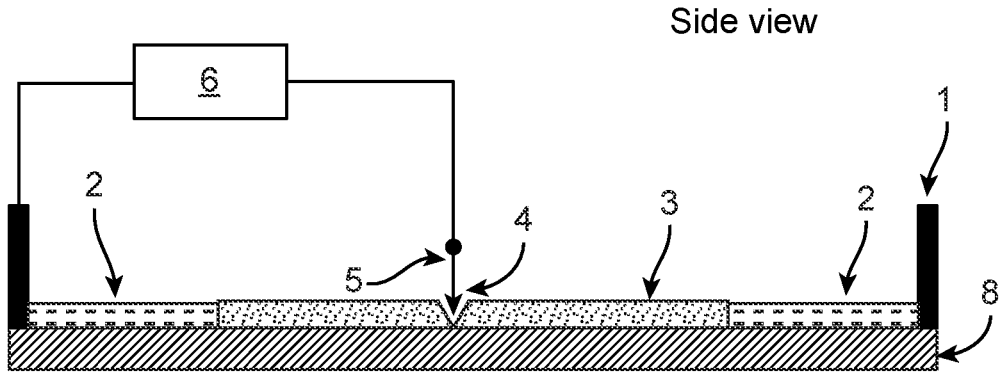
FIG. 2B provides a schematic representation of a side view of an exemplary device for effecting epitachophoresis.
Figure 3:
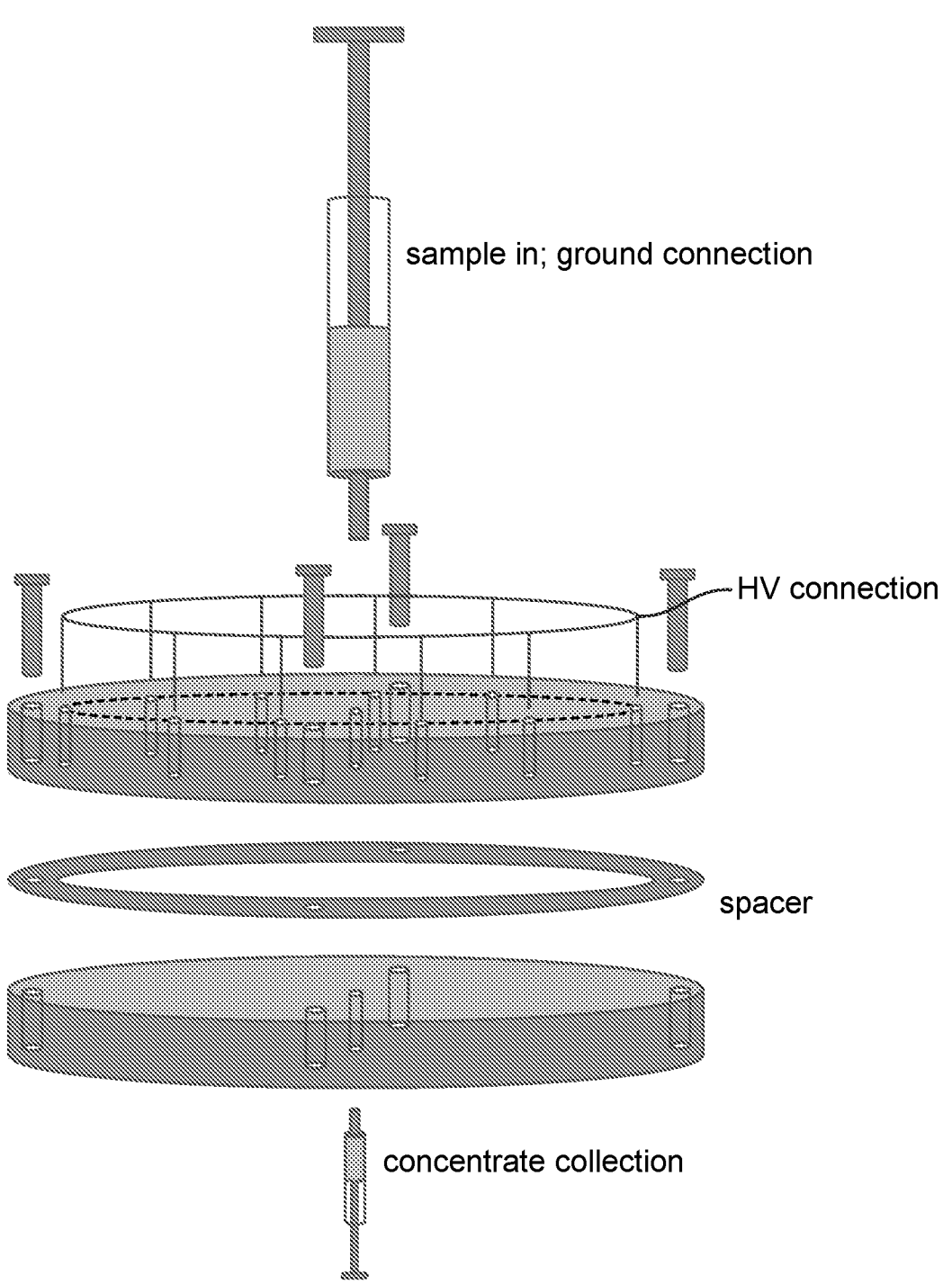
FIG. 3 provides a schematic representation of an exemplary device for effecting epitachophoresis.
Figure 4:
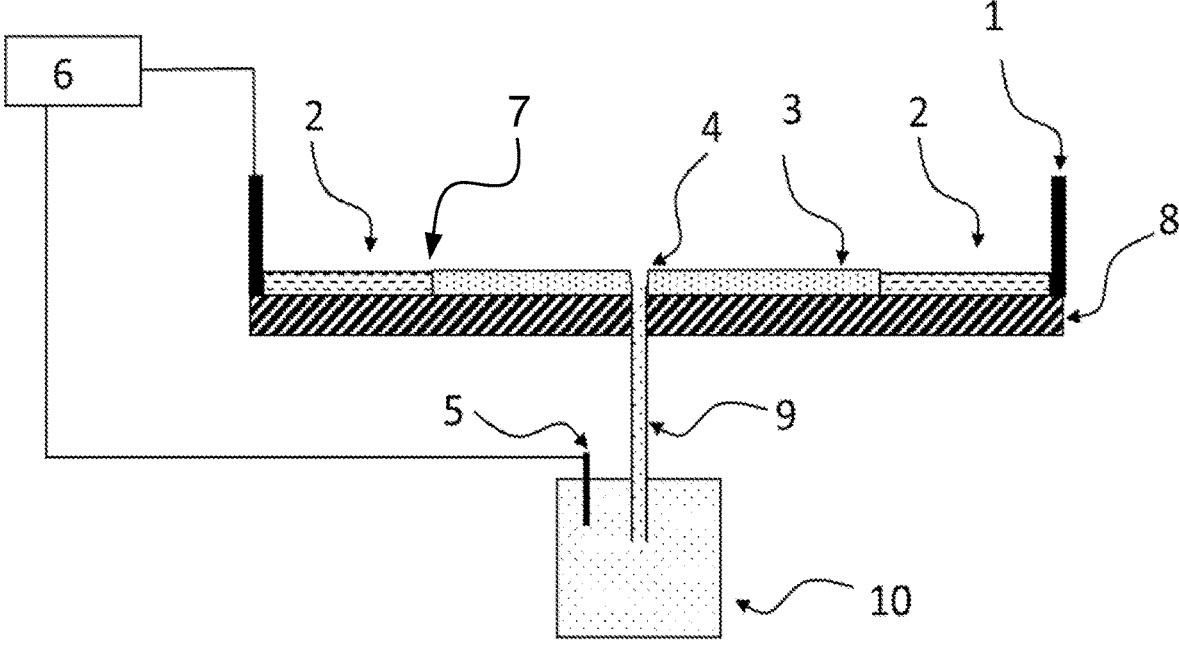
FIG. 4 provides a schematic representation of an exemplary device for effecting epitachophoresis.

Referring to FIG. 1-FIG. 3, two concentric disks are separated by a spacer, thereby forming a flat channel for epitachophoresis sample processing. Electric current is applied through multiple high voltage connections (HV connection) and the ground connection may be in the center of the system (see FIG. 1 and FIG. 3, for example). In some instances, the sample is injected into the device through an opening in the device, e.g., in the top or the side (see, for example, FIG. 3). Application of electricity focuses the target analyte of a sample as a concentric ring that migrates to the center of the disk, and the target analyte may then be collected through a syringe at the bottom of the device (see, for example, FIG. 3). As presented in FIG. 2A (top view) and FIG. 2B, an example of a device setup contains an outer circular electrode (1), terminating electrolyte (2), and leading electrolyte (3). In general, the diameter of the outer circular electrode (1) is about 10-200 mm and the diameter of the leading electrolyte ranges from a thickness (height) of about 10 μm to about 20 mm. The leading electrolyte may be stabilized by a gel, viscous additive, or otherwise hydrodynamically separated from the terminating electrolyte, such as, for example, by a membrane. The gel or hydrodynamic separation prevents mixing of the leading and terminating electrolytes during device operation. Also, in some devices mixing is prevented by using very thin (<100 um) layers of electrolytes, as is discussed further below.

Referring to FIG. 2A-FIG. 2B, in the center of the leading electrolyte is an electrolyte reservoir (4) with electrode (5). The assembly of the electrodes (1, 5) and electrolytes (2, 3) is placed on a flat, electrically insulating support (8). The electrolyte reservoir (4) is used for removal of the concentrated sample solution following a separation process, such as by pipetting the sample out of the reservoir, for example. Electrolyte reservoir (4) is also a sample collection reservoir. Outer circular electrode (1) may be disposed at the end of a circular channel in which the leading electrolyte (3) and terminating electrolyte (2) are disposed.

In an alternative arrangement (see FIG. 4) the center electrode (5) is moved to a leading electrolyte reservoir (10) connected with the concentrator by a tube (9). The tube (9) is connected directly or closed on one end by a semipermeable membrane (not shown). This arrangement facilitates the collection by stopping migration of large molecules according to the properties of the membrane used. This arrangement simplifies the sample collection and provides means of connecting the concentrator on-line to other devices, such as, for example, capillary analyzers, chromatography, PCR devices, enzymatic reactors, and the like. The tube (9) can also be used to supply a countercurrent flow of the leading electrolyte in an arrangement without a gel containing leading electrolyte.

In general, the gel for the leading electrolyte stabilization is formed by any uncharged material such as, for example agarose, polyacrylamide, *pullulans*, and the like. In some devices, the top surface is left open, or in some devices the top surface is closed, depending on the nature of the separation to be performed. If closed, the material used to cover the device is preferably a heat conducting, insulating material so as to prevent evaporation during the operation of an epitachophoresis device.

In general, the ring (circular) electrode is preferentially a gold-plated or platinum-plated stainless steel ring as this allows for maximum chemical resistance and electric field uniformity. Alternatively stainless steel and graphite electrodes may be used in some devices, particularly for disposable devices. Also, the ring (circular) electrode can be substituted with other structures that provide similar function, e.g., by an array of wire electrodes. Moreover, a 2-dimensional array of regularly spaced electrodes may additionally or alternatively be used in epitachophoresis devices. An array of regularly spaced electrodes in a circular orientation may also be used in epitachophoresis devices. Furthermore, other electrode configurations may also be used to effect different electric field shapes based on the desired sample separation (e.g., for directing the focused zones). Such configurations are described as polygon arrangements of electrodes. When divided into electrically separated segments, a switched electric field is created for time dependent shape of the driving electric field. Such an arrangement facilitates sample collection in some devices.

Figure 5:
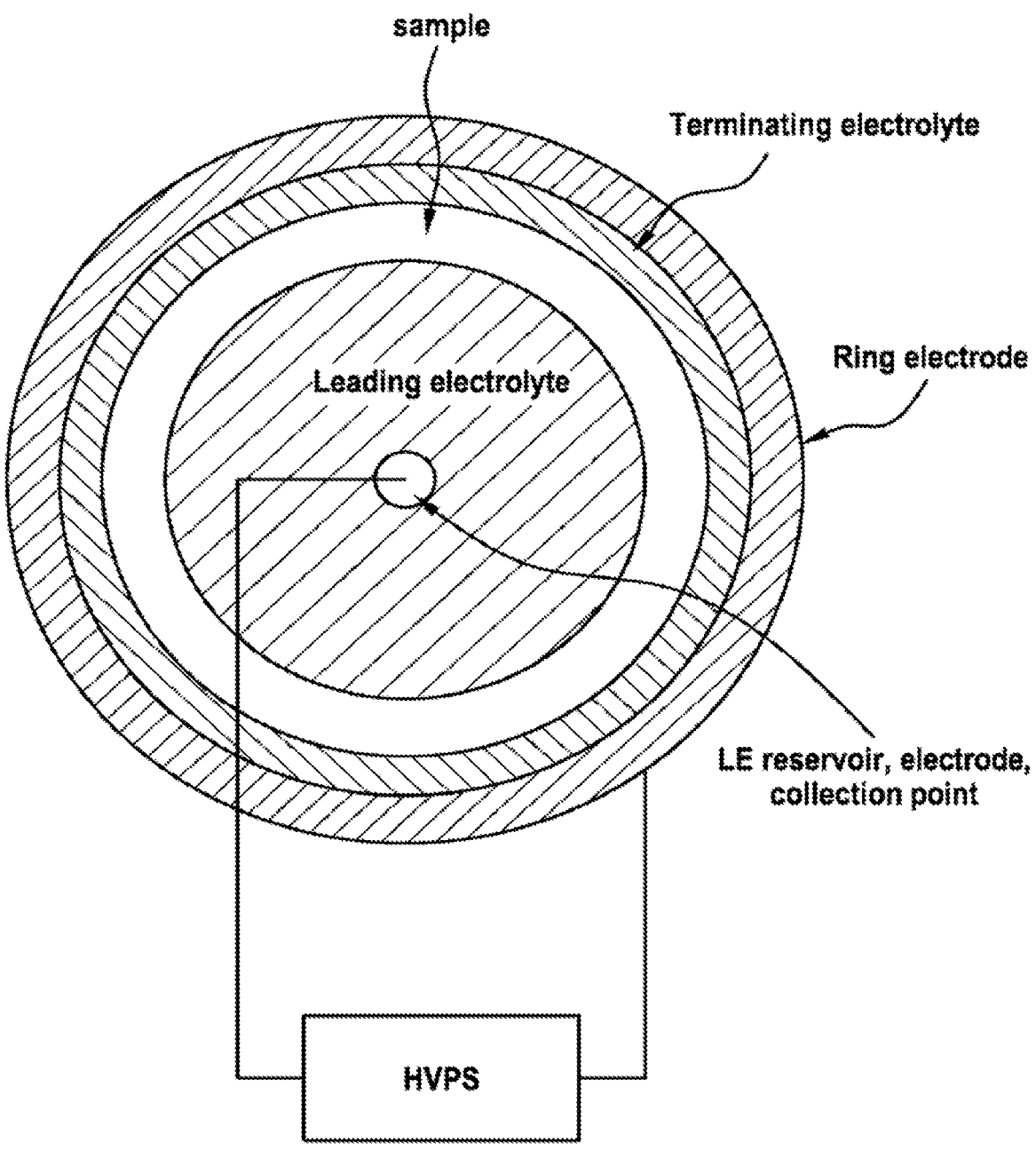
FIG. 5 provides a schematic representation of an exemplary device for effecting epitachophoresis wherein the sample is loaded in between loading the leading and terminating electrolytes.

Epitachophoresis devices, such as those of the designs presented in FIG. 1-FIG. 4, may be operated in either a two electrolyte reservoir arrangement, with the leading electrolyte followed by sample mixed with terminating electrolyte or with the sample mixed with the leading electrolyte followed by the terminating electrolyte, or in a three electrolyte reservoirs arrangement, as is presented in FIG. 5. In such an arrangement, the sample may be mixed with any conducting solution. Alternatively, when the sample contains suitable terminating ions the terminating electrolyte zone can be eliminated. Referring to FIG. 2A-FIG. 2B, upon filling the terminating electrolyte (2) area with a mixture of sample and suitable terminating electrolyte and turning on the electric power supply (6), the ions start moving towards the center electrode (5) and form zones at the boundary between leading and terminating electrolytes (7). The concentrations of the sample zones during the migration adjust according to general isotachophoretic principles [Foret, F., Krivankova, L., Bocek, P., *Capillary Zone Electrophoresis.*

*Electrophoresis Library*, (Editor Radola, B. J.) VCH, Verlagsgessellschaft, Weinheim, 1993.], the entire contents of which are incorporated herein by reference for all purposes. Thus, the low concentrated sample ions are concentrated and highly concentrated ones are diluted. In discontinuous electrolyte systems, the concentration of a zone is regulated by the concentration of the preceding one. A discontinuous electrolyte system may include different gel structure (or presence of gel), pH value of the buffer, ionic strength of the buffer, and/or ions. Thus, the concentration in zones of minor sample components will increase, but if there is something with a high concentration (higher than the leading zone) it will get diluted. Once the sample zone enters the electrolyte reservoir (4) the separation process is stopped, and the focused material is collected in the center of the device. In practice, final concentrations of migrating zones have a concentration comparable to that of the leading ion. Typically, concentration factors of anywhere from 2 to 1,000 or even more are achieved using epitachophoresis.

In a three electrolyte reservoir arrangement, the sample is applied in between the leading and terminating electrolytes (see, for example, FIG. 5), and such an arrangement may result in slightly faster sample concentration and separation as compared to a two electrolyte reservoir arrangement.

To avoid mixing, the leading electrolyte and the trailing electrolyte may be stabilized by a neutral (uncharged) viscous media, e.g., agarose gel (see, for example, FIG. 2A-FIG. 2B, (3), which represents the leading electrolyte optionally contained within a gel or hydrodynamically separated from the terminating electrolyte).

All common electrolytes that are used for isotachophoresis can be used with the present epitachophoresis devices when the leading ions have a higher effective electrophoretic mobility than that of the sample ion(s) of interest. The opposite is true for the selected terminating ions.

The device may be operated either in positive mode (separation/concentration of cationic species) or in negative mode (separation/concentration of anionic species). The most common leading electrolytes for anionic separation using epitachophoresis include, for example, chloride, sulfate, or formate, buffered to desired pH with a suitable base, e.g., histidine, TRIS, creatinine, and the like. Concentrations of the leading electrolyte for epitachophoresis for anionic separation range from 5 mM-1 M with respect to the leading ion. Terminating ions then often include MES, MOPS, HEPES, TAPS, acetate, glutamate and other anions of weak acids and low mobility anions. Concentrations of the terminating electrolyte for epitachophoresis in positive mode range from: 5 mM-10 M with respect to the terminating ion.

For cationic separation common leading ions for epitachophoresis include, for example: potassium, ammonium or sodium with acetate or formate being the most common buffering counterions. Reaction hydroxonium ion moving boundary then serves as a universal terminating electrolyte formed by any weak acid.

In both positive and negative modes, the increase of the concentration of the leading ion results in proportional increase of the sample zone at the expense of increased electric current (power) for a given applied voltage. Typical concentrations are in the 10-100 mM range; however, higher concentrations are also possible.

Furthermore, in cases where only zone electrophoretic separation is sufficient, the device can be operated with only one background electrolyte.

Current and/or voltage programming is suitable for adjusting the migration velocity of the sample. It should be noted that in this concentric arrangement, the cross section area changes during the migration and the velocity of the zone movement is not constant in time. Thus, this arrangement does not strictly follow the isotachophoretic principle where the zones migrate with constant velocities. According to the mode of operation of the electric power supply (6) three basic cases may be distinguished: 1. Separation at Constant Current; 2. Separation at Constant Voltage; and 3. Separation at Constant Power.

Figure 6:
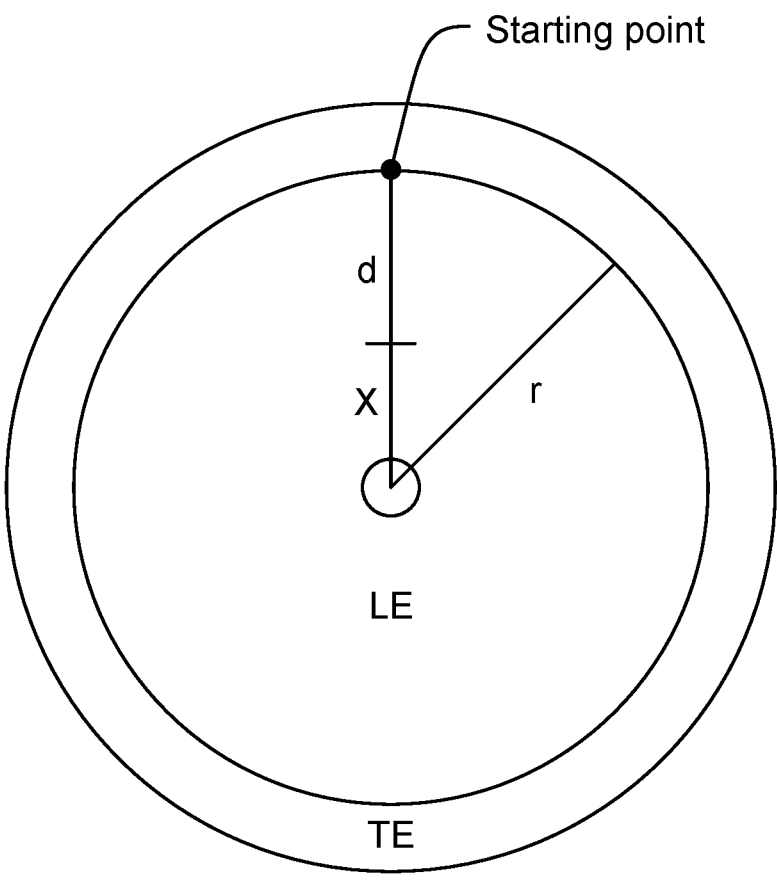
FIG. 6 provides a schematic representation of a device for effecting epitachophoresis and is referred to for equations described.

Variables for the equations described below are as follows: d=distance migrated (d<0; r>0); E=electric field strength; H=Electrolyte (gel) height; I=electric current; J=electric current density; x=electrolyte conductivity; r=radius; S=cross-section area (area between the two electrolytes); u=electrophoretic mobility; v=velocity; and X=length from the center electrode to epitachophoresis boundary. FIG. 6 shows the relationship of the variables d, r, and X in a device.

In the common mode of operation that uses constant electric current supplied by a high voltage power supply (HVPS), the migrating zone is accelerated as it moves closer to the center due to increasing current density. With regard to separation at constant current and using a device comprising a circular architecture, e.g., a device comprising one or more circular electrodes, the relative velocity at a distance, d, depends only on the mobility (conductivity) of the leading electrolyte, as is demonstrated by the derivation of the epitachophoresis boundary velocity at v at the distance d from the start radius r as follows:

General Equations:

$$U = IR \text{ or } E = J/\kappa \text{ (Ohm's Law)}$$
$$E = U/X \text{ (electric field strength)}$$
$$J = E\kappa \Rightarrow I = \frac{SU\kappa}{X}; R = X/\kappa S$$
$$v = uE$$
$$S = 2\pi X H$$

Epitachophoresis Boundary Velocity v at the distance d from the start with radius r:

$$v_{(d)} = u_L I/2\pi(r-d)h\kappa_L = \text{Constant}/(r-d)$$

The ETP device may also be operated at constant voltage or constant power. The velocity of the electromigration also accelerates during the analyses performed at constant voltage and constant power.

II. Volume Coupling Systems

Embodiments of the present invention may include systems that allow for volume coupling to concentrate components from a sample. These volume coupling systems may include adapting the devices of FIGS. 1-6 to include a second dimension for migration and a second volume for further concentration of the sample.

Figure 7:
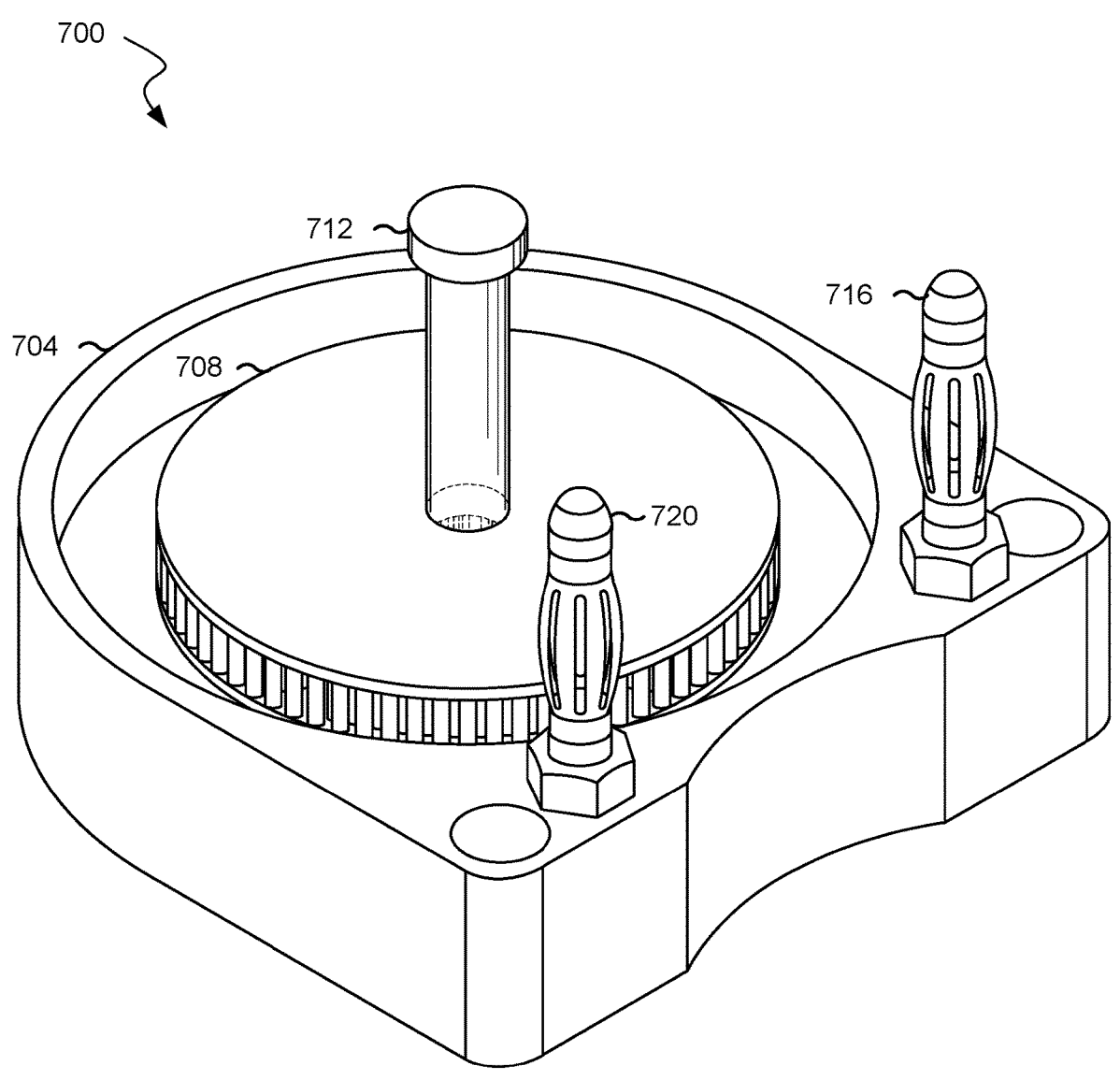
FIG. 7 shows a system for concentrating components in a sample using epitachophoresis according to embodiments of the present invention.

FIG. 7 shows a system 700 for concentrating components in a sample using epitachophoresis. System 700 includes a base 704. Base 704 may be electrically insulating support 8 of FIGS. 2A, 2B, and 4. Base 704 may define a cylindrical section, within which a manifold 708 is disposed on base 704. A pipette tip 712 may be disposed through the center of manifold 708. Manifold 708 may hold pipette tip 712 in place. Manifold 708 is optional. System 700 may include electrical leads 716 and 720. One of electrical leads 716 and 720 may be in electrical communication with a first electrode (not shown in FIG. 7). The first electrode may be a ring-shaped electrode at the outer edge of the cylindrical section in base 704. The first electrode may be any electrode described herein, including electrode 1 of FIGS. 2A, 2B, and 4. The other of electrical leads 716 and 720 may be in electrical communication with a second electrode (not shown in FIG. 7). The second electrode may provide voltage to the bottom end of pipette tip 712. The second electrode may be similar to electrode 5 of FIGS. 2A, 2B, and 4, except the position of the electrode may be further downstream of a sample collection point (e.g., where the pipette tip is placed).

A terminating electrolyte may be disposed between the manifold 708 and toward the outer edge of the cylindrical section in base 704. Terminating electrolyte may be any terminating electrolyte described herein, including terminating electrolyte 2 in FIGS. 2A, 2B, and 4. A leading electrolyte may be in the center of manifold 708 and contact the terminating electrolyte. The leading electrolyte and the terminating electrolyte may or may not contact each other at the edge of manifold 708. The outer edge of the leading electrolyte may be a circle or on a circle, and the terminating electrolyte may be an annulus or the edges of the terminating electrolyte may trace an annulus. The leading electrolyte may be any leading electrolyte described herein, including leading electrolyte 3 in FIGS. 2A, 2B, and 4.

Figure 8:
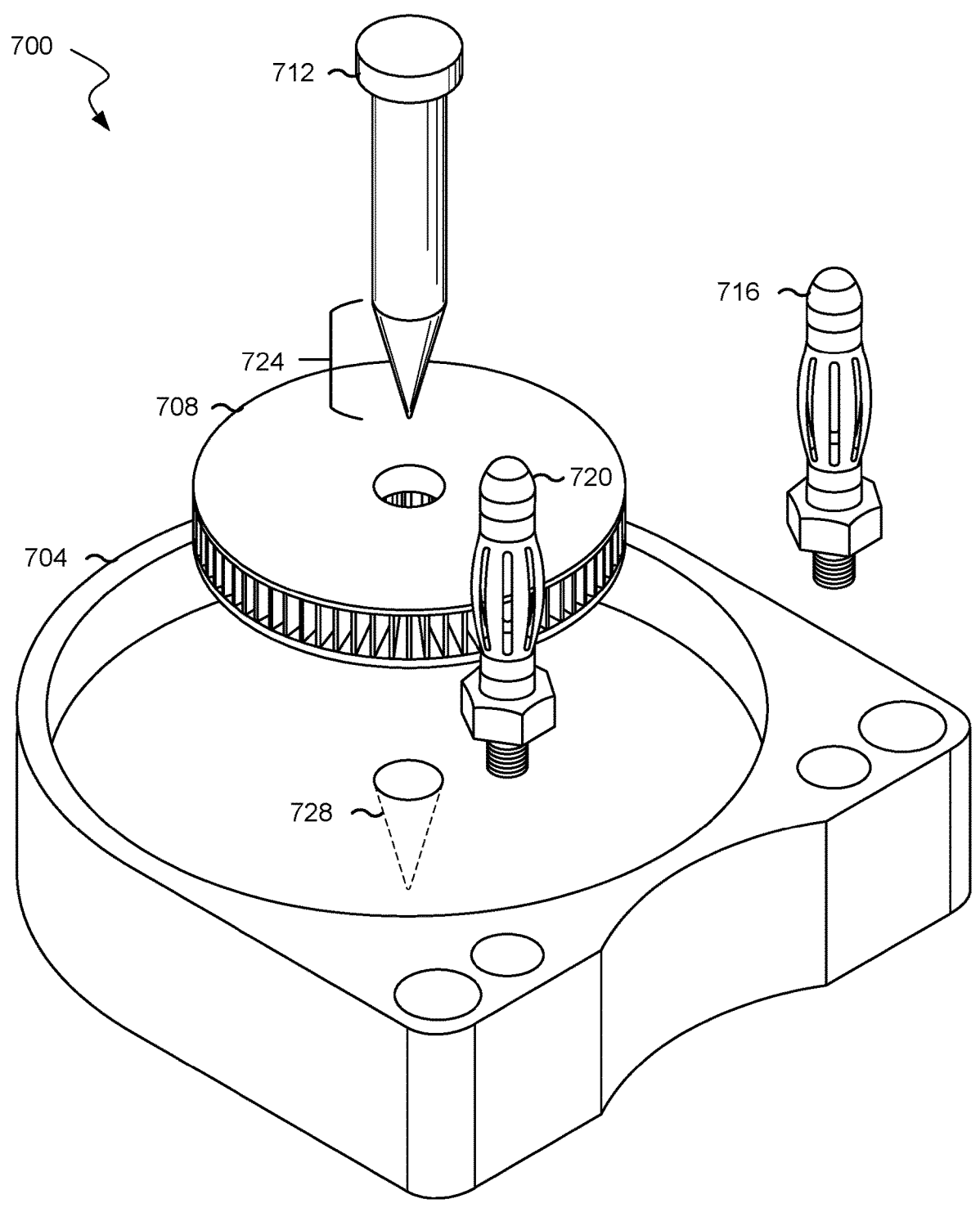
FIG. 8 shows an exploded view of a system for concentrating components in a sample using epitachophoresis according to embodiments of the present invention.

FIG. 8 shows system 700 in an exploded view. Pipette tip 712 has a conical portion 724, not visible in FIG. 7. Conical portion 724 fits within cavity 728 within base 704. Cavity 728 is also conical in shape. Cavity 728 may be slightly larger than conical portion 724 of pipette tip 712, resulting in an annular space between base 704 and pipette tip 712 when pipette tip 712 is inside cavity 728, as in FIG. 7. Cavity 728 differs from electrolyte reservoir 4 in FIGS. 2A, 2B, and 4. Cavity 728 is formed below the surface of a planar section for the electrolytes in base 704. Additionally, unlike electrolyte reservoir 4 in FIG. 4, cavity 728 is configured to receive pipette tip 712 and create annular flow to conical portion 724, rather than the entirety of electrolyte reservoir 4 acting as a conduit to a sample collection vessel.

Figure 9:
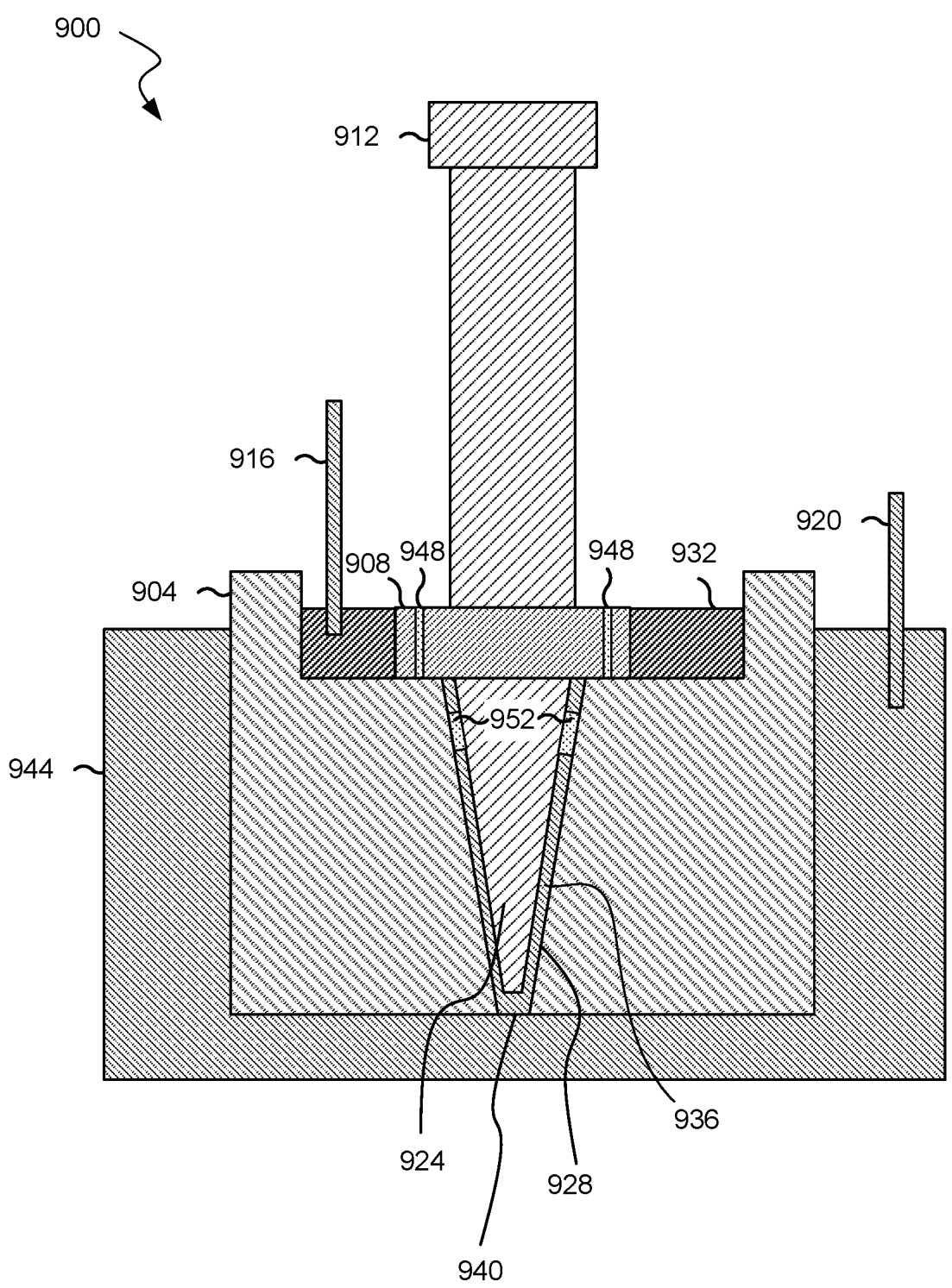
FIG. 9 illustrates a cross section through a system for concentrating components in a sample using epitachophoresis according to embodiments of the present invention.

FIG. 9 illustrates a cross section through a pipette tip in a system 900 similar to system 700. System 900 includes a base 904. Manifold 908 is disposed in a section defined by base 904. Pipette tip 912 is shown going through base 904. Pipette tip 912 is disposed in cavity 928, which is defined by base 904. Pipette tip 912 allows for collection of components not possible with manifold 908. An annular space 936 is formed between cavity 928 and pipette tip end 924. First electrode 916 is in first channel 932. First channel 932 is defined by base 904 and manifold 908. Second electrode 920 is disposed in reservoir 944, which is in fluid communication with annular space 936. Fluid in reservoir 944 may be separated from fluid in annular space 936 by a membrane 940. Membrane 940 may allow ions to pass through but may not allow analytes or other components in a sample to pass through. Membrane 940 may be any membrane described herein. Membrane 940 may have a diameter in from 1 to 2 mm, 2 to 3 mm, 3 to 4 mm, 4 to 5 mm, 5 to 7 mm, 7 to 10 mm, or greater than 10 mm.

First channel 932 may include a first electrolyte and a sample, which can form a first mixture. Components of the sample may pass through manifold 908, which may include a second electrolyte. The components may form a focused band 948 in passing through manifold 908 and/or the second electrolyte. Focused band 948 may move radially inward. Annular space 936 may include the second electrolyte. The voltage difference applied to first electrode 916 and second electrode 920 may drive a charged component from first channel 932 to annular space 936 to above membrane 940. The charged component may enter pipette tip end 924 through suction from a pipette through pipette tip end 924. The components may form a focused band 952 within annular space 936. Focused band 952 may move away from the top of system 900 and toward membrane 940 and/or an orifice at the bottom of pipette tip end 924. Focused band 952 may move radially inward.

In some embodiments, a system for concentrating components in a sample may include a base defining a first channel and a cavity. The base may be any base described herein, including base 704 and base 904. The base may be defined from a single piece of material. The cavity may be any cavity described herein, including cavity 728 and cavity 928.

The first channel may include any first channel described herein, including first channel 932. The first channel may be circular. The first channel is in fluid communication with the cavity. For example, components in a liquid may be able to travel from the first channel to the cavity within the liquid. An outer diameter of the first channel may be greater than a first outer diameter at the top of the cavity. The outer diameter of the first channel may be the diameter of the cylindrical recess shown in base 704 in FIG. 7 and FIG. 8.

The cavity may include a conical shape with the first outer diameter being greater than a second outer diameter at the bottom of the cavity. The narrower portion of the conical shape may be at the bottom of the system. As used herein, "bottom" and "top" refer to the orientation of the system during normal operation. Conical shape includes the shape of a cone or substantially similar to a cone. The sides of the cavity may taper to a point (i.e., a vertex). Substantially similar may include a shape that the horizontal cross section of the shape at any point has a maximum length (e.g., diameter) that is within 5%, 10%, or 15% of the dimensions of a cone defined by the same vertex and the opening of the cavity. The cone may be a right circular cone. In some embodiments, the conical shape may not include the vertex. For example, the conical shape may be truncated to include a bottom surface, which may be a circle. For example, the conical shape may have a cross section similar to cavity 928 in FIG. 9 with membrane 940 being one end of the conical shape. In some embodiments, the surface of the base may be conical. The cavity may have a depth of 5 to 10 mm, 10 to 15 mm, 15 to 20 mm, 20 to 30 mm, 30 to 40 mm, 40 to 50 mm, or greater than 50 mm.

In some embodiments, the cavity may have a cylindrical section on top of the conical section. In this manner, the cavity may have a shape that is similar to the vessel (e.g., pipette tip), which has a conical and a cylindrical portion.

The system may further include a first electrode disposed in the first channel. The first electrode may be any electrode described herein, including first electrode 916. In some embodiments, the first electrode may be ring-shaped. The system may further include a second electrode. The second electrode may be any electrode described herein, including second electrode 920. The second electrode is configured to be in closer electrical communication with the cavity than with the first channel when the first channel and the cavity contain an electrolyte. Closer electrical communication may refer to the resistance being lower or the current being higher given the same voltage applied. The cavity may be physically closer to the second electrode than the first channel is to the second electrode. When the second electrode is disposed in a liquid that contacts the cavity and the first channel, the amount of liquid between the second electrode and the cavity is less than the amount of liquid between the first channel and the second electrode. The second electrode may be ring-shaped, a plate, or a rod.

The first channel is characterized by a first volume. The first volume may be considered to be the volume of a liquid that can be contained by first channel. For example, in FIG. 9, the first volume of first channel 932 may not include the volume taken by manifold 908. The first volume may be 0.25 ml or less, 0.25 to 0.50 ml, 0.50 to 0.75 ml, 0.75 to 1.0 ml, 1.0 to 2.5 ml, 2.5 to 5.0 ml, 5.0 to 7.5 ml, 7.5 to 10.0 ml, 10.0 to 12.5 ml, 12.5 to 15.0 ml, 15.0 to 30.0 ml, 30.0 ml to 50.0 ml, or more than 50 ml.

The cavity is configured to receive a vessel and to form a second channel when the vessel is disposed in the cavity. The vessel may be any vessel described herein, including pipette tip 112 and pipette tip 912. In some embodiments, the vessel may be a trocar or a needle of a syringe. The vessel may define a cannula through which fluid may enter from the cavity. The vessel may be configured to hold a sample collection volume of 1 to 500 µl, including 1 to 10 µl, 10 to 50 µl, 50 to 100 µl, 100 to 200 µl, 200 to 300 µl, 300 to 400 µl, 400 to 500 µl, or greater than 500 µl. The vessel may be held in place by a manifold. In some embodiments, the vessel may be held in place through supports attached to the base. In other embodiments, supports external to the base may hold the vessel in place. For example, the supports may be an arm of a robotic handling system.

The second channel may be an annular space, including annular space 936. The annular space may be defined by a surface of the base and a surface of the vessel when the vessel is disposed in the cavity. The second channel is characterized by a second volume. The first volume is greater than the second volume. The first volume may be 5 to 10 times, 10 to 20 times, 20 to 50 times, 50 to 100 times, or more than 100 times greater than the second volume. In some embodiments, the surface of the base and the surface of the vessel are concentric. The annular space may be the space between the two concentric surfaces.

In some embodiments, the cavity is below a bottom surface of the base defining the first channel. For example, as shown in FIG. 8 and FIG. 9, the first channel may be a first recessed portion of the base, and the cavity may be a second recessed portion in the first recessed portion. The bottom surface of the base defining the first channel may contact or intersect the surface of the base defining the second channel. The surfaces may intersect at a circle.

In some embodiments, the system may include a membrane between the cavity and the second electrode. The membrane may be a semi-permeable membrane. The membrane may be membrane 940 shown in FIG. 9. The membrane may allow particles smaller than a certain size to pass through. Components in a biological sample that are intended to be analyzed may not pass through the membrane.

In some embodiments, the system may include a reservoir. The second electrode may be disposed in the reservoir. The reservoir may be any reservoir described herein, including reservoir 944. The reservoir may contain an electrolyte, including the leading electrolyte. The reservoir may be separated from the cavity by the membrane. The same electrolyte may be present in the reservoir and the cavity. An electric field from the second electrode disposed in the reservoir may be propagated to the cavity through the reservoir.

In some embodiments, the system may include a power supply in electrical communication with the first electrode and the second electrode. In some embodiments, the system may include a computer configured to control the power supply. The power supply may deliver a constant voltage, a constant current, or a constant power.

In some embodiments, the system may include an in vitro diagnostic assay device, including any in vitro diagnostic assay described herein. The assay device may include a detector configured to detect a component in a sample. The detector may include optical, detectors, electrochemical detectors, or any detectors described herein.

In some embodiments, the system may include the vessel. In some embodiments, the system may include the vessel disposed in the cavity. In other embodiments, the system may include the vessel not disposed in the cavity.

In some embodiments, the system may include a first electrolyte disposed in the first channel. The first electrolyte may be the terminating electrolyte. The system may include a second electrolyte, which may be the leading electrolyte. The second electrolyte may be disposed in a gel in the first channel and also disposed in the cavity. The system may include the gel. The electrolytes and gel may be any disclosed herein.

In some embodiments, the system may include a manifold. The manifold may define a plurality of channels that have an outlet into the second channel. The plurality of channels defined by the manifold may be between the first channel and the second channel.

In some embodiments, the base may define a plurality of structures extending into the cavity. The plurality of structures may include a first structure and a second structure on the opposite side of the cavity as the first structure. The distance between the first structure and the second structure may be a diameter of the vessel. The length of the structure may be the second thickness in the second channel. The structures may hold or support the vessel within the cavity.

Figures 10A, 10B, 10C, 10D, 10E:
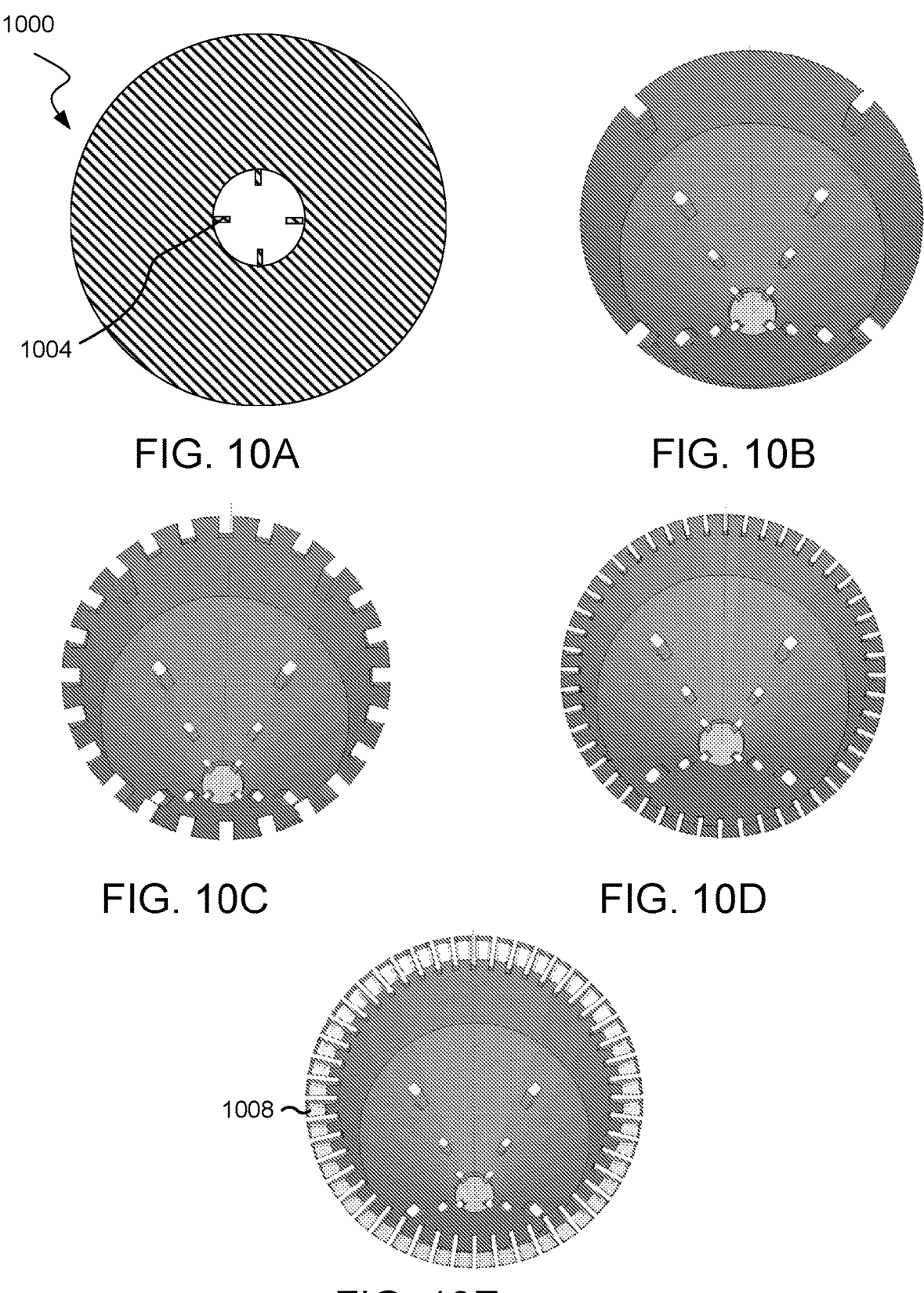
FIGS. 10A (bottom view), 10B, 10C, 10D, and 10E (top view) illustrate supports for holding a pipette tip according to embodiments of the present invention.

FIG. 10A shows the bottom view of a base 1000 having four supports including support 1004. The supports may be the plurality of structures extending into the cavity. Support 1004 is a protrusion from the circular cavity. The four supports are equally spaced apart (90 degrees between adjacent supports). Each support may be identical to the other supports. The supports may be rectangular in shape. In some embodiments, the support may be triangular, pyramidal, trapezoidal, or rounded in shape. The support may have a length that is from 2% to 5%, 5% to 10%, 10% to 15%, 15% to 20%, 20% to 25%, 25% to 33%, or 33% to 40% of the diameter of the cavity. The distance between a support to the support on the opposite side of the cavity may be an outer diameter of a vessel (e.g., a pipette tip). The supports at the top of the cavity may number 4 to 8, 8 to 10, 10 to 16, 16 to 20, 20 to 30, or 30 to 50. Additional supports may be present at different depths in the cavity.

FIGS. 10B, 10C, 10D, and 10E illustrate top views of different numbers of supports at the top of the cavity and supports at different depths in the cavity. FIGS. 10B, 10C, 10D, and 10E each show four supports at each depth below the top of the cavity. The number of supports at each depth may be any number provided for supports at the top of the cavity, and the number may be the same or different as the number of supports at the top of the cavity. Supports may be provided at different depth levels. For example, FIGS. 10B, 10C, 10D, and 10E shows support at three depth levels. Different depth levels are possible, including 2 to 5 and 5 to 10. Adjacent depth levels may be separated by the same or different vertical distance. FIG. 10E shows a recessed portion 1008 of the top part of the base between supports.

Recessed portion 1008 may be a ramp down into the cavity to allow for more fluid flow than if there portion was not recessed.

III. Example Methods

Figure 11:
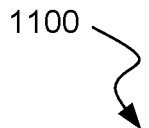
FIG. 11 is a flowchart of an example process for concentrating a component from a sample according to embodiments of the present invention.
Figure 11:
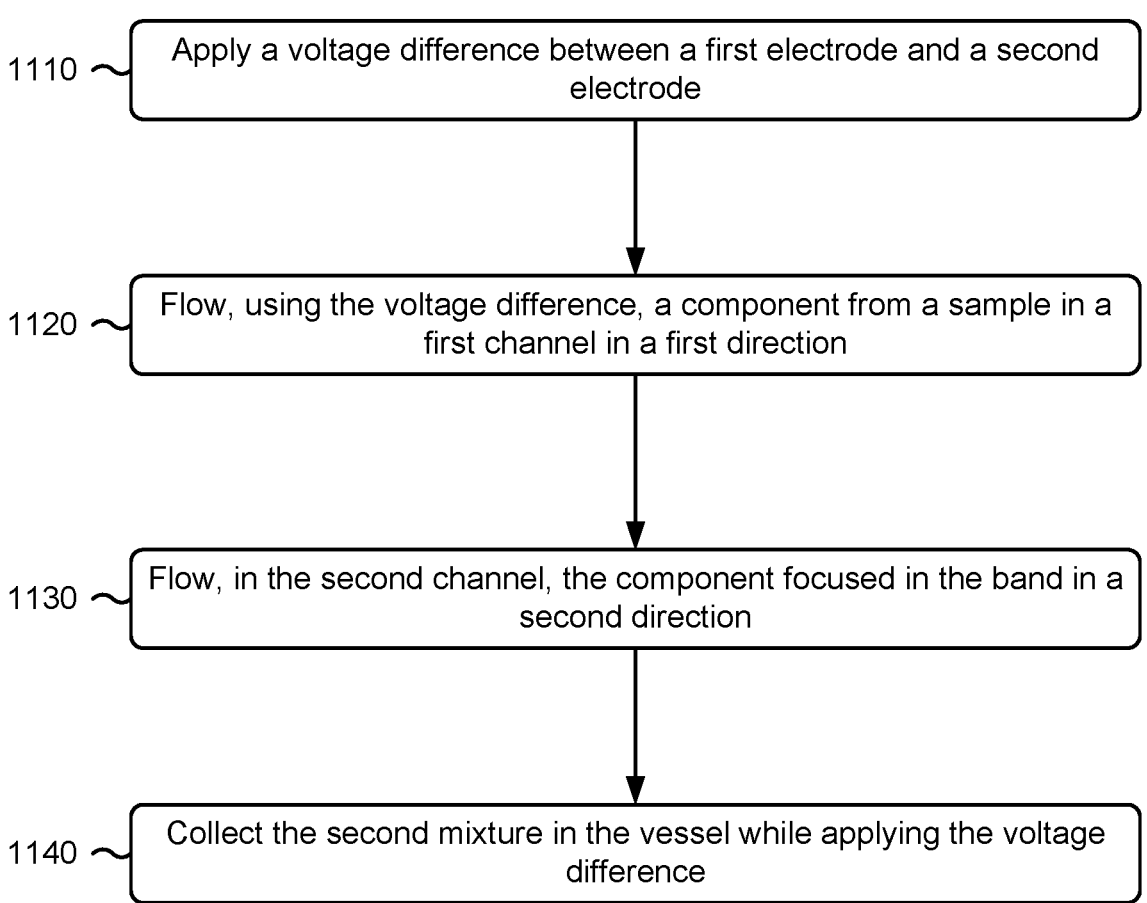

FIG. 11 is a flowchart of an example process 1100 associated with volume coupling in epitachophoresis. Process 1100 may concentrate a component from a sample. Process 1100 may be for ETP-based isolation/purification. The sample may be any sample described herein. The component may include a target nucleic acid, a target microbe, a biomarker, or a target analyte. The sample may include multiple components. The sample may be from a subject. The sample may be a mixed sample, with material from more than one source. The sample may include an ETP upper marker.

In some embodiments, one or more process blocks of FIG. 11 may be performed by an epitachophoresis device (e.g., system 900 of FIG. 9). In some embodiments, one or more process blocks of FIG. 11 may be performed by another device or a group of devices separate from or including the epitachophoresis device. Additionally, or alternatively, one or more process blocks of FIG. 11 may be performed by one or more parts of system 1200, such as logic system 1230, processor 1250, memory 1235, external memory 1240, storage device 1245, and/or treatment device 1260. Process 1100 may include additional embodiments, such as any single embodiment or any combination of embodiments described below and/or in connection with one or more other processes described elsewhere herein.

At block 1110, process 1100 may include applying a voltage difference between a first electrode and a second electrode. The first electrode may be disposed in a first mixture including a first electrolyte and the sample. In some examples, the first mixture may be in first channel 932 of FIG. 9. The second electrode may be disposed in a second electrolyte. The second electrolyte may be disposed in a gel in the first channel. The gel may be within manifold 908 or within the area of manifold 908. The first electrolyte may be different from the second electrolyte. The second electrolyte may be contained in a gel. The second electrolyte may be hydrodynamically separated from the first electrolyte. The first electrolyte and the second electrolyte may be separated by a membrane. The epitachophoresis device may apply the voltage difference between the first electrode and the second electrode.

The first electrode may be circular. The first electrode may be a ring and may be disposed at the edge of the channel, which may also be circular. As examples, the first electrode may be any electrode described herein, including first electrode 916 of FIG. 9. The second electrode may be any electrode described herein, including second electrode 920.

The voltage difference may be a constant voltage. In some embodiments, the voltage difference may be the result of a constant current applied. In some embodiments, the voltage difference applied may be the result of a constant power applied. The voltage may range from about 10 V to about 10 kV with electric powers ranging from about 1 mW to about 100 W.

At block 1120, process 1100 may include flowing, using the voltage difference, the component in a first channel in a first direction. The first channel may be any channel described herein, including first channel 932. The first direction may be away from the first electrode and to a second channel. The component may be focused into a band. The focused bands may be sections where the target analytes are concentrated within the first electrolyte or the second electrolyte. The target analytes in a particular focused band may include ions with the same or similar mobility in an applied electric field. The band may be ring-shaped and be referred to as a focused zone, such as the focused zone in FIG. 1. The focusing may result from the applied voltage and the electrolytes. The first mixture may be characterized as having a first thickness perpendicular to the first direction. The first thickness may be a height. For example, the first thickness may be the height of the first mixture in first channel 932. The first thickness may be the vertical dimension of focused band 948 shown in FIG. 9.

At block 1130, process 1100 may include flowing, in the second channel, the component focused in the band in a second direction. The band may flow in the first channel, exit the first channel, and then enter the second channel. The second electrolyte may be in the second channel. The second direction may be from the first channel to an orifice of a vessel. The second channel may be an annular space. The second channel may include any second channel described herein, including annular space 936. A second mixture including the component and the second electrolyte in the second channel may be characterized as having a second thickness perpendicular to the second direction. The first thickness may be greater than the second thickness. The thickness of the fluid may decrease as the fluid moves from the first channel to the second channel. The fluid may include the component and either of the first or second electrolytes. The second thickness may be a height. The second thickness may be the thickness of focused band 952 shown in annular space 936, the thickness may be perpendicular to a wall defining annular space 936. The amount of the component in the second mixture may be the same as amount of the component in the first mixture.

In embodiments, the annular space is defined by an outer surface of the vessel. The vessel may include a conical shape. The second channel may be defined by a first conical surface and a second conical surface. A first conical surface may be the outer surface of the vessel. The second conical surface may be a surface of the base.

Process 1100 may include flowing, in the second channel, the component focused in the band in the second direction comprises reducing the radius of the band and flowing the component in the direction of gravity. The second direction may not be only in the direction of gravity. The second direction may be angled downward such that the second direction is the sum of a non-zero vector in the downward direction (direction of gravity) and one or more other vectors. The second direction may point directly at a vertex of a cone formed by the first conical surface or the second conical surface. In some embodiments, the second direction may point directly at a cone, which has a surface within the annular space.

In embodiments, the first channel and the second channel may each defined by a base. The base may be any base described herein, including base 904. In some embodiments, process 1100 may include flowing the component in a plurality of channels between the first channel and the second channel. The plurality of channels may be defined by a manifold, which may include manifold 908.

In embodiments, the first direction may not be collinear with the second direction. The first direction may be horizontal and toward the center of a circle forming the outside of the first channel. The second direction may be toward the center of the circle but at a location below the bottom surface of the first channel.

The first channel may be characterized by a first volume. The first volume may be defined as the maximum volume of a liquid that can be disposed in the first channel. The volume of the first channel may be determined based on the area of the bottom surface of the first channel and the height of a sidewall of the first channel. The second channel may be characterized by a second volume. The second volume may be the volume of the annular space. The first volume may be at least 10 times greater than the second volume. In some embodiments, the first volume may be 5 to 10 times, 10 to 50 times, 50 to 100 times, 100 to 150 times, or greater than 150 times greater than the second volume.

In embodiments, the second channel may have a length in the second direction of at least 2 mm. The length in the second direction may be 2 to 5 mm, 5 to 10 mm, 10 to 15 mm, or greater than 15 mm.

At block 1140, process 1100 may include collecting the second mixture in the vessel while applying the voltage difference. Collecting the mixture in the vessel may include flowing the second mixture into the vessel in a third direction against gravity. The concentration of the component in the second mixture in the vessel may be higher than the concentration of the component in the sample, including 2 to 5 times, 5 to 10 times, 10 to 100 times, 100 to 500 times, 500 to 1,000 times, 1,000 to 2,000 times, or more than 1,000 times greater.

In embodiments, the sample may include additional components from the sample, and the additional components may be focused into additional bands. For example, the component is a first component, and the sample may further include a second component. The second component may be focused into a second band in the first channel. The method may further include flowing, using the voltage difference, the second component in the first channel. The method may also include flowing, in the second channel, the second component focused into the second band in the second direction. Process 1100 may include collecting the second component in the vessel.

Although FIG. 11 shows example blocks of process 1100, in some embodiments, process 1100 may include additional blocks, fewer blocks, different blocks, or differently arranged blocks than those depicted in FIG. 11. Additionally, or alternatively, two or more of the blocks of process 1100 may be performed in parallel.

IV. Example Systems

Figure 12:
FIG. 12 illustrates a measurement system according to embodiments of the present invention.
Figure 12:
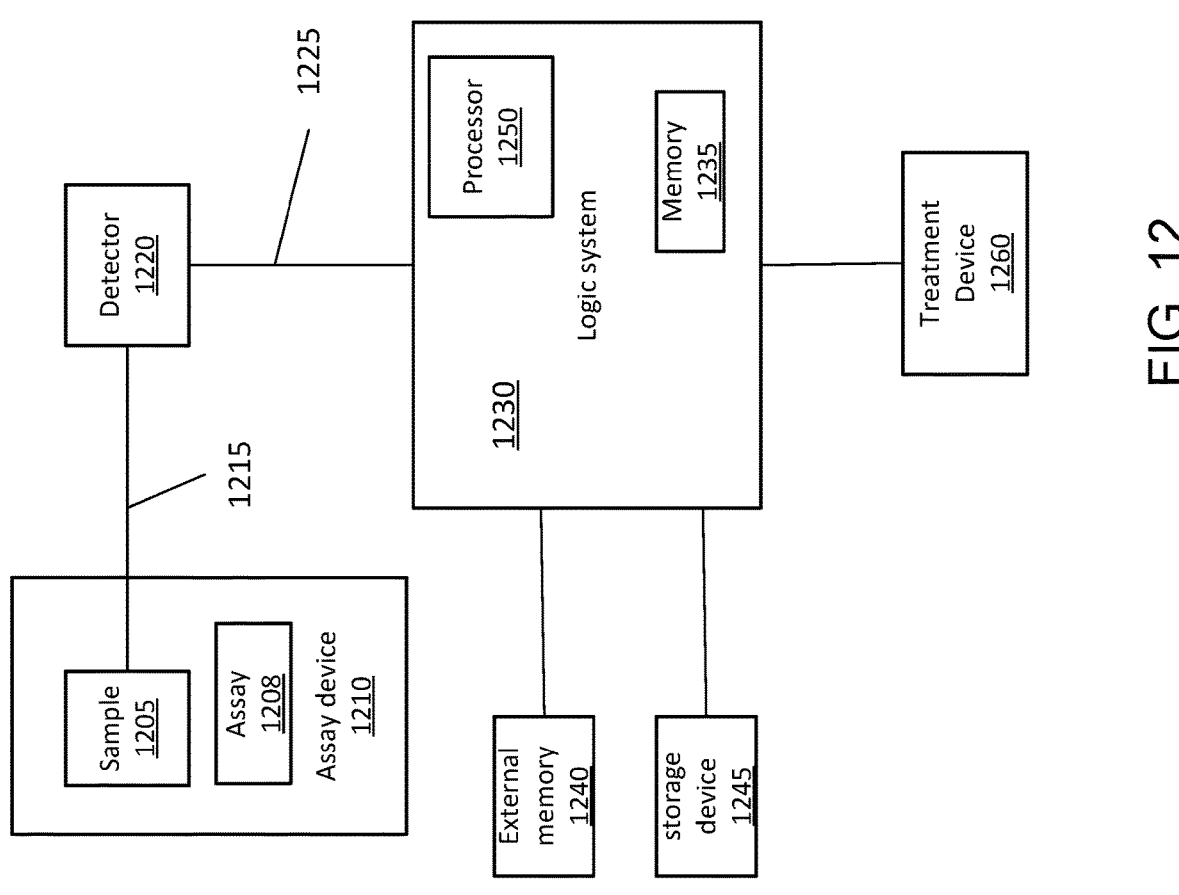

FIG. 12 illustrates a measurement system 1200 according to an embodiment of the present disclosure. The system as shown includes a sample 1205, such as cell-free DNA molecules within an assay device 1210, where an assay 1208 can be performed on sample 1205. For example, sample 1205 can be contacted with reagents of assay 1208 to provide a signal of a physical characteristic 1215. An example of an assay device can be a flow cell that includes probes and/or primers of an assay or a tube through which a droplet moves (with the droplet including the assay). Assay device 1210 may include multiple modules, including any epitachophoresis (ETP) device described herein. The ETP device can concentrate or separate sample 1205, and that concentrated sample may be sent to another module in the assay device. The other module may perform an in vitro diagnostic assay.

Physical characteristic 1215 (e.g., a fluorescence intensity, a voltage, or a current), from the sample is detected by detector 1220. Detector 1220 can take a measurement at intervals (e.g., periodic intervals) to obtain data points that make up a data signal. In one embodiment, an analog-to-digital converter converts an analog signal from the detector into digital form at a plurality of times. Assay device 1210 and detector 1220 can form an assay system, e.g., a sequencing system that performs sequencing according to embodiments described herein. A data signal 1225 is sent from detector 1220 to logic system 1230. As an example, data signal 1225 can be used to determine sequences and/or locations in a reference genome of DNA molecules. Data signal 1225 can include various measurements made at a same time, e.g., different colors of fluorescent dyes or different electrical signals for different molecule of sample 1205, and thus data signal 1225 can correspond to multiple signals. Data signal 1225 may be stored in a local memory 1235, an external memory 1240, or a storage device 1245.

Logic system 1230 may be, or may include, a computer system, ASIC, microprocessor, graphics processing unit (GPU), etc. It may also include or be coupled with a display (e.g., monitor, LED display, etc.) and a user input device (e.g., mouse, keyboard, buttons, etc.). Logic system 1230 and the other components may be part of a stand-alone or network connected computer system, or they may be directly attached to or incorporated in a device (e.g., a sequencing device) that includes detector 1220 and/or assay device 1210.

Logic system 1230 may also include software that executes in a processor 1250. Logic system 1230 may include a computer readable medium storing instructions for controlling measurement system 1200 to perform any of the methods described herein. For example, logic system 1230 can provide commands to a system that includes assay device 1210 such that sequencing or other physical operations are performed. Such physical operations can be performed in a particular order, e.g., with reagents being added and removed in a particular order. Such physical operations may be performed by a robotics system, e.g., including a robotic arm, as may be used to obtain a sample and perform an assay. Moreover, in some embodiments, the ETP device may be used with liquid handling robots that may optionally be used to effect downstream analysis of a sample that may have been focused and/or collected from said device.

Measurement system 1200 may also include a treatment device 1260, which can provide a treatment to the subject. Treatment device 1260 can determine a treatment and/or be used to perform a treatment. Examples of such treatment can include surgery, radiation therapy, chemotherapy, immunotherapy, targeted therapy, hormone therapy, and stem cell transplant. Logic system 1230 may be connected to treatment device 1260, e.g., to provide results of a method described herein. The treatment device may receive inputs from other devices, such as an imaging device and user inputs (e.g., to control the treatment, such as controls over a robotic system).

Figure 13:
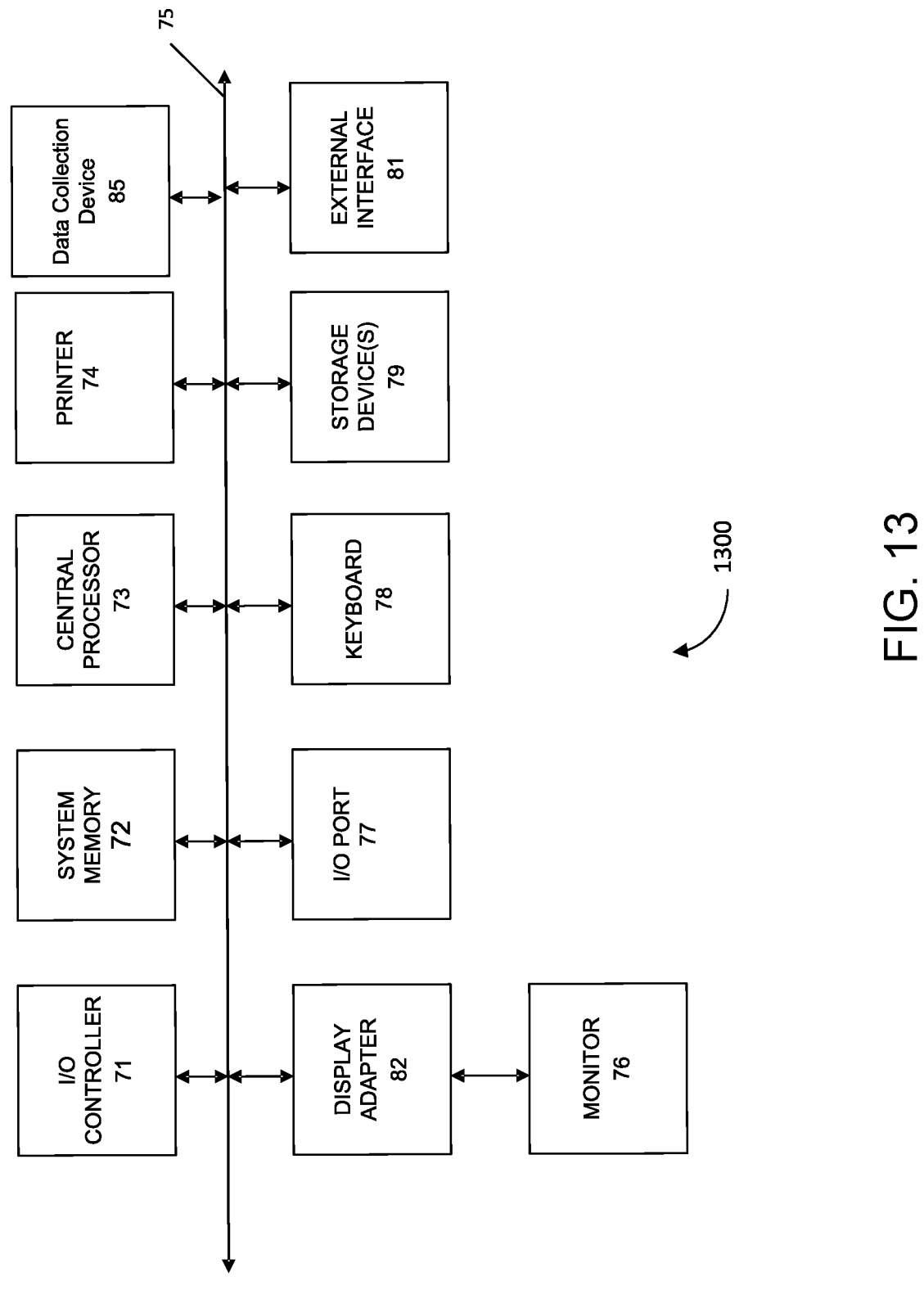
FIG. 13 shows a computer system according to embodiments of the present invention.

Any of the computer systems mentioned herein may utilize any suitable number of subsystems. Examples of such subsystems are shown in FIG. 13 in computer system 1300. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 13 are interconnected via a system bus 75. Additional subsystems such as a printer 74, keyboard 78, storage device(s) 79, monitor 76 (e.g., a display screen, such as an LED), which is coupled to display adapter 82, and others are shown. Peripherals and input/output (I/O) devices, which couple to I/O controller 71, can be connected to the computer system by any number of means known in the art such as input/output (I/O) port 77 (e.g., USB, Lightning). For example, I/O port 77 or external interface 81 (e.g. Ethernet, Wi-Fi, etc.) can be used to connect computer system 1300 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81, by an internal interface, or via removable storage devices that can be connected and removed from one component to another component. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware circuitry (e.g. an application specific integrated circuit or field programmable gate array) and/or using computer software with a generally programmable processor in a modular or integrated manner. As used herein, a processor can include a single-core processor, multi-core processor on a same integrated chip, or multiple processing units on a single circuit board or networked, as well as dedicated hardware. Based on the disclosure and teachings provided herein, a person of ordinary skill in the art will know and appreciate other ways and/or methods to implement embodiments of the present disclosure using hardware and a combination of hardware and software.

Any of the software components or functions described in this application may be implemented as software code to be executed by a processor using any suitable computer language such as, for example, Java, C, C++, C #, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk) or Blu-ray disk, flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective step or a respective group of steps. Although presented as numbered steps, steps of methods herein can be performed at a same time or at different times or in a different order that is logically possible. Additionally, portions of these steps may be used with portions of other steps from other methods. Also, all or portions of a step may be optional. Additionally, any of the steps of any of the methods can be performed with modules, units, circuits, or other means of a system for performing these steps.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The above description of example embodiments of the present disclosure has been presented for the purposes of illustration and description and are set forth so as to provide those of ordinary skill in the art with a complete disclosure and description of how to make and use embodiments of the present disclosure. It is not intended to be exhaustive or to limit the disclosure to the precise form described nor are they intended to represent that the experiments are all or the only experiments performed. Although the disclosure has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the disclosure being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover, reference to a "first" or a "second" component does not limit the referenced component to a particular location unless expressly stated. The term "based on" is intended to mean "based at least in part on."

The claims may be drafted to exclude any element which ray be optional. As such, this statement is intended to serve as antecedent basis for use of such exclusive terminology as "solely", "only", and the like in connection with the recitation of claim elements, or the use of a "negative" limitation.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within embodiments of the present disclosure. The upper and lower limits of these smaller ranges may independently be included or excluded in the range, and each range where either, neither, or both limits are included in the smaller ranges is also encompassed within the present disclosure, subject to any specifically excluded limit in the stated range. Where the stated range includes one or both of the limits, ranges excluding either or both of those included limits are also included in the present disclosure.

All patents, patent applications, publications, and descriptions mentioned herein are hereby incorporated by reference in their entirety for all purposes as if each individual publication or patent were specifically and individually indicated to be incorporated by reference and are incorporated herein by reference to disclose and describe the methods and/or materials in connection with which the publications are cited. None is admitted to be prior art.

What is claimed is:

1. A method of concentrating a component from a sample, the method comprising:

applying a voltage difference between a first electrode and a second electrode, wherein:

the first electrode is disposed in a first mixture comprising a first electrolyte and the sample, the second electrode is disposed in a second electrolyte, and the first electrolyte is different from the second electrolyte;

flowing, using the voltage difference, the component in a first channel in a first direction, wherein:

the first direction is away from the first electrode and to a second channel that intersects the first channel, the component is focused into a band, the band while in the first channel is characterized as having a first thickness perpendicular to the first direction;

flowing, in the second channel, the component focused in the band in a second direction, wherein:

the second electrolyte is in the second channel, the second channel is an annular space formed between a cavity and a vessel, the second direction is from the intersection with the first channel to an orifice of the vessel, the second channel characterized as having a second thickness that is perpendicular to the second direction and extends from a surface of the cavity to an opposing surface of the vessel, a second mixture comprising the component and the second electrolyte in the second channel, and the first thickness is greater than the second thickness; and collecting the second mixture in the vessel while applying the voltage difference, wherein the concentration of the component in the second mixture in the vessel is higher than the concentration of the component in the sample.

2. The method of claim 1, wherein:

the component is a first component, the sample comprises a second component, the band is a first band, and the second component is focused into a second band in the first channel, the method further comprising:

flowing, using the voltage difference, the second component in the first channel, and flowing, in the second channel, the second component focused into the second band in the second direction.

3. The method of claim 2, further comprising collecting the second component in the vessel.

4. The method of claim 1, wherein the first thickness is a height.

5. The method of claim 1, wherein the annular space is defined by an outer surface of the vessel.

6. The method of claim 1, wherein the first channel and the second channel are each defined by a base.

7. The method of claim 1, wherein the first direction is not collinear with the second direction.

8. The method of claim 1, wherein the vessel comprises a conical shape.

9. The method of claim 1, wherein the second electrolyte is disposed in a gel in the first channel.

10. The method of claim 1, wherein the band is ring-shaped.

11. The method of claim 1, wherein:

the first channel is characterized by a first volume, the second channel is characterized by a second volume, and the first volume is at least 10 times greater than the second volume.

12. The method of claim 1, wherein the second channel has a length in the second direction of at least 2 mm.

13. The method of claim 1, wherein collecting the second mixture in the vessel comprises flowing the second mixture into the vessel in a third direction against gravity.

14. The method of claim 1, wherein flowing, in the second channel, the component focused in the band in the second direction comprises reducing the radius of the band and flowing the component in the direction of gravity.

15. A system for concentrating components in a sample, the system comprising:

a base defining a first channel and a cavity, wherein the cavity comprises a conical shape with a first outer diameter at a top of the cavity being greater than a second outer diameter at a bottom of the cavity;

a first electrode disposed in the first channel; and a second electrode;

wherein:

the first channel is in fluid communication with the cavity, an outer diameter of the first channel is greater than the first outer diameter at the top of the cavity, the second electrode is configured to be in closer electrical communication with the cavity than with the first channel when the first channel and the cavity contain an electrolyte, the first channel is characterized by a first volume, the cavity is configured to receive a vessel and to form a second channel when the vessel is disposed in the cavity, the second channel is an annular space, the annular space is defined by a surface of the base and a surface of the vessel when the vessel is disposed in the cavity, the second channel is characterized by a second volume, and the first volume is greater than the second volume.

16. The system of claim 15, wherein the surface of the base and the surface of the vessel are concentric.

17. The system of claim 15, wherein the surface of the base is conical.

18. The system of claim 15, wherein the cavity is below a bottom surface of the base defining the first channel.

19. The system of claim 15, further comprising a membrane between the cavity and the second electrode.

20. The system of claim 15, wherein:

the base defines a plurality of structures extending into the cavity, the plurality of structures includes a first structure and a second structure on the opposite side of the cavity as the first structure, and the distance between the first structure and the second structure is a diameter of the vessel.

* * * * *